United States Patent [19]

Haslanger et al.

[11] Patent Number: 4,749,688

[45] Date of Patent: Jun. 7, 1988

[54] USE OF NEUTRAL METALLOENDOPEPTIDASE INHIBITORS IN THE TREATMENT OF HYPERTENSION

[75] Inventors: Martin F. Haslanger, Ridgewood; Edmund J. Sybertz, Jr., South Orange, both of N.J.

[73] Assignee: Schering Corporation, Kenilworth, N.J.

[21] Appl. No.: 876,610

[22] Filed: Jun. 20, 1986

[51] Int. Cl.$^4$ .............................................. A61K 37/43
[52] U.S. Cl. ...................................... 514/19; 514/18; 514/17
[58] Field of Search ............................ 514/17, 18, 19

[56] References Cited

FOREIGN PATENT DOCUMENTS

| | | |
|---|---|---|
| 0012401 | 6/1980 | European Pat. Off. . |
| 0037231 | 10/1981 | European Pat. Off. . |
| 0046953 | 3/1982 | European Pat. Off. . |
| 0079522 | 5/1983 | European Pat. Off. . |
| 0079022 | 5/1983 | European Pat. Off. . |
| 0083172 | 7/1983 | European Pat. Off. . |
| 0097050 | 12/1983 | European Pat. Off. . |
| 0117429 | 9/1984 | European Pat. Off. . |
| 2095682 | 10/1982 | United Kingdom . |
| 2159160A | 11/1985 | United Kingdom . |
| 2167748A | 5/1986 | United Kingdom . |

OTHER PUBLICATIONS

T. Baum et al., Eur. J. Pharm., 94 (1983), pp. 85–91.
M. Wyvratt et al., Med. Res. Rev., 5 (1985), pp. 483–531.
P. Needleman et al., N. Engl. J. Med., 314 (1986), pp. 828–834.
M. Cantin et al., Scientific Amer., 254 (1986), pp. 76–81.
B. P. Rogues et al., Eur. J. Biochem., 139 (1984), pp. 267–274.
R. A. Mumford et al., Biochem. Biophys. Res. Commun., 109 (1982), pp. 1303–1307.
B. P. Rogues et al., J. Med. Chem., 26 (1983), pp. 60–65.
B. P. Rogues, J. Med. Chem., 28 (1985), pp. 1158–1169.

Primary Examiner—Delbert R. Phillips
Attorney, Agent, or Firm—Anita W. Magatti; Gerald S. Rosen; Stephen I. Miller

[57] ABSTRACT

The method of treating hypertension with neutral metalloendopeptidase (NMEP) inhibitors, NMEP inhibitors in combination with atrial peptides, and NMEP inhibitors in combination with angiotensin converting enzyme inhibitors, as well as pharmaceutical compositions therefor, are disclosed.

16 Claims, No Drawings

USE OF NEUTRAL METALLOENDOPEPTIDASE INHIBITORS IN THE TREATMENT OF HYPERTENSION

The present invention relates to the treatment of hypertension with neutral metalloendopeptidase inhibitors.

In particular, neutral metalloendopeptidase (NMEP) inhibitors alone or in combination with atrial peptides may be used to treat certain types of hypertension, and NMEP inhibitors may be used to enhance the antihypertensive activity of angiotensin converting enzyme inhibitors.

A second aspect of the invention relates to pharmaceutical compositions comprising NMEP inhibitors, to pharmaceutical compositions comprising a combination of an NMEP inhibitor and an atrial peptide, and to pharmaceutical compositions comprising an NMEP inhibitor and an angiotensin converting enzyme inhibitor, all for use in treating hypertension.

BACKGROUND

Human hypertension represents a disease of multiple etiologies. Included among these is a sodium and volume dependent low renin form of hypertension. Drugs that act to control one aspect of hypertension will not necessarily be effective in controlling another.

Enkephalin, a natural opiate receptor agonist, is known to produce analgesia, and it is also known that enkephalin is inactivated by a neutral metalopeptidase (EC 3.4.24.11) frequency referred to as enkephalinase or enkephalinase A. Various NMEP inhibitors have been discovered which, by their inhibition of this enzyme elicit an analgesic effect. To date, no significant cardiovascular activity has been attributed to NMEP inhibitors. The NMEP inhibitor thiorphan was found to inhibit peripheral ACE, but to have little direct cardiovascular activity in its own right: blood pressure and heart rate were not affected. See T. Baum, et al, "Enkephalinase A Inhibition by Thiorphan: Central and Peripheral Cardiovascular Effects", *Eur. J. Pharm.*, 94(1983), pg 85–91.

One class of drugs which is known to be effective in treating some types of hypertension is angiotensin converting enzyme (ACE) inhibitors, which compounds are useful in blocking the rise in blood pressure caused by increases in vascular resistance and fluid volume due to the formation of angiotensin II from angiotensin I. For a review of ACE inhibitors, see M. Wyvratt and A. Patchett, "Recent Developments in the Design of Angiotensin Converting Enzyme Inhibitors" in *Med. Res. Rev.* Vol. 5, No. 4 (1985) pp. 483–531, incorporated herein by reference.

It has recently been discovered that the heart secretes a series of peptide hormones called atrial natriuretic factors (ANF) which help to regulate blood pressure, blood volume and the excretion of water, sodium and potassium. ANF were found to produce a short-term reduction in blood pressure and to be useful in the treatment of congestive heart failure. See P. Needleman et al, "Atriopeptin: A Cardiac Hormone Intimately Involved in Fluid, Electrolyte and Blood-Pressure Homeostasis", *N. Engl. J. Med.*, 314, 13 (1986) pp. 828–834, and M. Cantin et al in "The Heart as an Endocrine Gland", *Scientific American*, 254 (1986) pg. 76–81.

DETAILED DESCRIPTION

We have surprisingly found that NMEP inhibitors lower blood pressure under conditions where ACE inhibitors are relatively ineffective, for example in salt-dependent hypertension. A second aspect of the invention is that administration of the combination of NMEP inhibitors and exogenous atrial peptides provides improved magnitude and duration of the antihypertensive effects when compared to the use of atrial peptides alone. A third unexpected aspect of the invention is that administration of combinations of NMEP inhibitors and ACE inhibitors provides an antihypertensive effect greater than the activity of either NMEP inhibitor or the ACE inhibitor alone.

The present invention therefore relates to treating hypertension with an NMEP inhibitor, with an NMEP inhibitor in combination with an atrial peptide, and with an NMEP inhibitor in combination with an ACE inhibitor, which methods comprise administering to a mammal in need of such treatment an antihypertensive effective amount of the NMEP inhibitor, the combination of NMEP inhibitor and atrial peptide, or the combination of NMEP inhibitor and ACE inhibitor. The drug or combination of drugs is preferably administered in a pharmaceutically acceptable carrier, e.g. for oral or parenteral administration. The combinations of drugs may be co-administered in a single composition, or components of the combination therapies may be administered separately. Where the components are administered separately, any convenient combination of dosage forms may be used, e.g. oral NMEP inhibitor/oral ACE inhibitor, oral NMEP inhibitor/parenteral atrial peptide, parenteral NMEP inhibitor/oral ACE inhibitor, parenteral NMEP inhibitor/parenteral atrial peptide.

When the components of a combination of an NMEP inhibitor and an atrial peptide are administered separately, it is preferred that the NMEP inhibitor be administered first.

The present invention also relates to a pharmaceutical composition comprising an NMEP inhibitor for use in treating hypertension, to a pharmaceutical composition comprising both an NMEP inhibitor and an ACE inhibitor, and to a pharmaceutical composition comprising both an NMEP inhibitor and an atrial peptide.

The NMEP inhibitors contemplated for use in this invention are exemplified by, but not limited to:

thiorphan (N-[(R,S)-3-mercapto-2-benzylpropanoyl]-glycine) and related compounds, see B. P. Rogues et al, *Eur. J. Biochem.*, 139 (1984) 267–274;

carboxyalkyl inhibitors such as (S)-HomoPhe-[N]-L-Phe-Gly (See R. A. Mumford, et al, *Biochem. Biophys. Res. Commun.*, 109 (1982) 1303–1307) and N-[(R,S)-2-carboxy-3-phenypropanoyl]-L-leucine (See B. P. Rogues et al, *J. Med. Chem.*, 26 (1983) 60–65);

hydroxamic acid inhibitors such as N-[3(R,S)-(N-formyl-N-hydroxyamino)-1-oxo-2-benzylpropyl]glycine, N-[3(R,S)-[(hydroxyamino)carbonyl]-2-benzyl-1-oxopropyl]glycine and N-[3(R,S)-[(hydroxyamino)carbonyl]-2-benzyl-1-oxopropyl]-L-alaine (See B. P. Rogues, *J. Med. Chem.*, 28 (1985) 1158–1169);

compounds disclosed in U.S. Pat. No. 4,610,816 having the formula

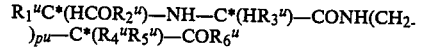

and the racemates, enantiomers and diastereoisomers thereof and the pharmaceutically acceptable salts thereof wherein:

$R_1^u$ is alkyl having from 1 to 6 carbon atoms, adamantylmethyl, cycloakylmethyl having from 4 to 8 carbon atoms or $A^u—X_m{}^u—C_nH_{2nu}$— wherein $X^u$ is oxygen or sulfur, $A^u$ is phenyl which may be substituted with the group, $Y^u$, wherein $Y^u$ is halogen, hydroxy, trifluoromethyl, alkoxy having from 1 to 6 carbon atoms, alkyl having from 1 to 6 carbon atoms, 2- and 3-furanyl, 2- and 3-thienyl, or phenyl [which may be substituted with halogen, hydroxy, trifluoromethyl, alkoxy having from 1 to 6 carbon atoms or alkyl having from 1 to 6 carbon atoms] benzyl [the phenyl ring of which may be substituted with the group, Y, as defined herein], 1- and 2-naphthyl, 2- and 3-furanyl or 2- and 3-thienyl; $m^u$ is 0 or 1 and $n^u$ is 0, 1, 2, 3, or 4;

$R_2^u$ and $R_6^u$ may be the same or different and are hydroxy, alkoxy having from 2 to 8 carbon atoms, $B^u—X_m{}^u—C_nH_{2nu}—O—$ wherein $B^u$ is phenyl [which may be substituted with the group, $Y^u$, as defined herein] or 1- and 2-naphthyl, $X^u$, $m^u$, and $n^u$ are as defined herein provided that when $n^u=0$, $m^u=0$, —OCH$_2$OCO—alkyl having from 3 to 8 carbon atoms, —OCH$_2$CO—phenyl [the phenyl ring of which may be substituted with the group, $Y^u$, as defined herein], 1-glyceryl,

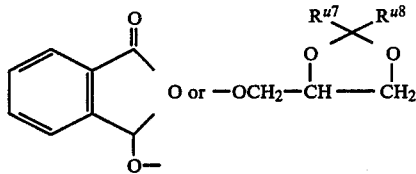

wherein $R_7^u$ is hydrogen, alkyl having from 1 to 6 carbon atoms, or phenyl which may be substituted with the group, $Y^u$, as defined herein, and $R_8^u$ is hydrogen or alkyl having from 1 to 6 carbon atoms;

$R_2^u$ may also be —NR$_7^u$R$_8^u$ wherein $R_7^u$ and $R_8^u$ are as defined herein;

$R_3^u$ is alkyl having from 1 to 6 carbon atoms, cycloalkylmethyl having from 4 to 8 carbon atoms, 2- and 3-thienylmethyl, 2- and 3-furanylmethyl, 1- and 2-naphthylmethyl, or benzyl, the phenyl ring of which may be substituted with the group, $Y^u$, as defined herein;

$R_4^u$ is $D^u—C_nH_{2nu}—O_{mu}$— wherein $D^u$ is hydrogen, alkyl having from 1 to 4 carbon atoms or phenyl which may be substituted with the group, $Z^u$, wherein $Z^u$ is halogen, hydroxy, trifluoromethyl, alkoxy having from 1 to 6 carbon atoms, or alkyl having from 1 to 6 carbon atoms; $m^u$ and $n^u$ are as defined herein;

$R_4^u$ may also be —NR$_5^u$COR$_7^u$ (wherein $R_5^u$ and $R_7^u$ are defined herein), NR$_5^u$CO$_2$R$_9^u$ (wherein $R_5^u$ is defined herein and $R_9^u$ is alkyl having from 1 to 6 carbon atoms or phenyl which may be substituted with the group, $Y^u$, defined herein), provided that $p^u$ is 1 or 2;

$R_5^u$ is hydrogen or alkyl having from 1 to 6 carbon atoms; and $p^u$ is 0, 1 or 2.

The most preferred values for the above defined groups are as follows:

$R_1^u$ is benzyl or p-phenylbenzyl; $R_2^u$ is hydroxy, 2-phenoxyethoxy, 1-glyceryl,

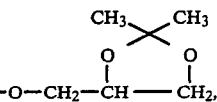

pivaloyloxymethoxy or benzyloxy; $R_3^u$ is benzyl or p-phenylbenzyl; $R_4^u$ is hydrogen, methyl or benzyl; $R_5^u$ is hydrogen; $R_6^u$ is hydroxy; and $p^u$ is 1. Preferred compounds having the above structural formula are:

N-[N-[(L-1-carboxy-2-phenylethyl)]-L-phenylalanyl]-β-alanine and

N-[N-[L-1-(2,2-dimethyl-1-oxopropoxy)methoxy]-carbonyl]-2-phenylethyl]-L-phenylalanyl]-β-alanine, (2,2-dimethyl-1-oxopropoxy)methyl ester;

Compounds disclosed in European Patent Application No. 117,429 having the formula:

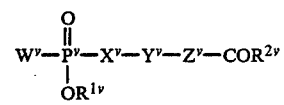

wherein $R^{1v}$ is hydrogen, alkyl having from 1 to 6 carbon atoms,

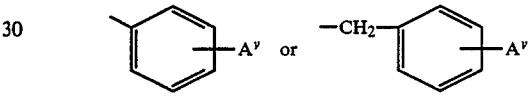

in which $A^v$ is hydrogen, halogen, hydroxy, nitro, trifluoromethyl, alkoxy having from 1 to 6 carbon atoms, alkyl having from 1 to 6 carbon atoms, 2- or 3-thienyl or phenyl which may be substituted with halogen, hydroxy, nitro, trifluoromethyl, alkoxy having from 1 to 6 carbon atoms, or alkyl having from 1 to 6 carbon atoms;

$W^v$ is $R^{1v}$ or $OR^{1v}$ wherein $R^{1v}$ is as defined above;

$X^v$ is —(CH$_2$)$_{pv}$—CHR$^3$— or —CHR$^3$—(CH$_2$)$_{pv}$— wherein $p^v$ is 0 or 1, and $R^{3v}$ is 2- or 3-thienylmethyl, 3-indolylmethyl, alkyl having from 1 to 6 carbon atoms, cycloalkyl having from 3 to 7 carbon atoms, cycloalkylmethyl having from 4 to 8 carbon atoms,

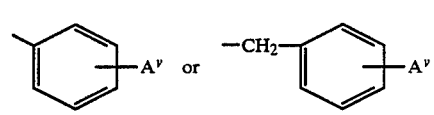

in which $A^v$ is as defined above,

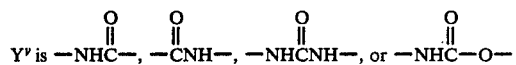

$Z^v$ is o-, m- or p-phenylene, —(CHR$^{4v}$)$_{rv}$— [wherein $r^v$ is 1, 2, 3, or 4 and $R^{4v}$ is independently chosen from hydrogen, alkyl having from 1 to 6 carbon atoms, hydroxy, alkoxy having from 1 to 6 carbon atoms, cycloalkyl having from 3 to 7 carbon atoms, cycloalkylmethyl having from 4 to 8 carbon atoms, 3-indolylmethyl, hydroxymethyl, 2-(methylthio)ethyl,

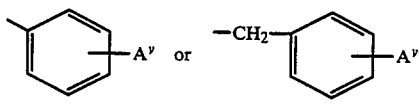

in which $A^v$ is as defined above] or $-B_{q^v}{}^v-B'^v-B''^v-$ [wherein $q^v$ is 0 or 1, one of the groups, $B^v$, $B'^v$ or $B''^v$ is

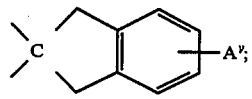

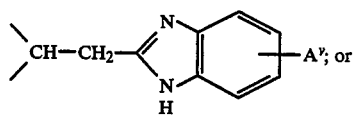

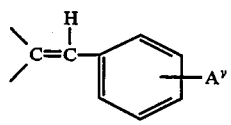

in which $A^v$ is as defined above and the remaining $B^v$, $B'^v$ and/or $B''^v$ is $-CH_2-$],

[with the following provisos:
when $W^v$ is $OR^{1v}$ and $Y^v$ is $-NHCO-$, $r^v$ may not be 1;
when $Y^v$ is

$r^v$ cannot be 1;
when $Y^v$ is

$Z^v$ may also be $-CR^{av}=CR^{bv}-$
wherein $R^{av}$ and $R^{bv}$ may be the same or different and are chosen from hydrogen, alkyl having from 1 to 6 carbon atoms, cycloalkyl having from 3 to 7 carbon atoms, cycloalkylmethyl having from 4 to 8 carbon atoms, 3-indolyl-methyl, hydroxymethyl, 2-(methylthio)ethyl, or together with the carbon atoms to which they are attached form a cycloalkenylene ring having from 5 to 8 carbon atoms;

$R_2^v$ is hydroxy, alkoxy having from 1 to 6 carbon atoms,

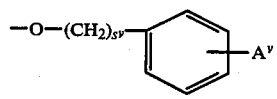

[wherein $s^v$ is 0, 1, 2, or 3],

[wherein $R^{5v}$ and $R^{6v}$ may be the same or different and are hydrogen or alkyl having from 1 to 6 carbon atoms, and $R_7^v$ is

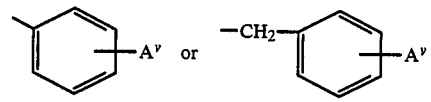

or alkyl having from 1 to 6 carbon atoms],

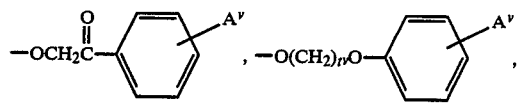

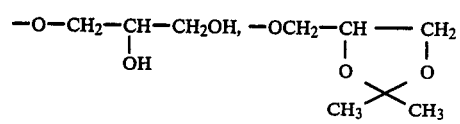

[wherein $t^v$ is 1 or 2],

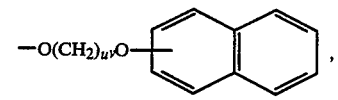

[wherein $u^v$ is 1 or 2],

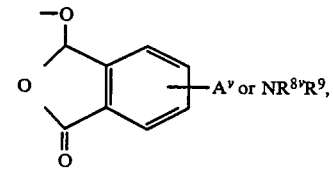

wherein $R^{8v}$ is

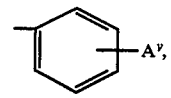

$R^{9v}$ is hydrogen or alkyl having from 1 to 6 carbon atoms, and wherein $A^v$ in the groups defined for $R_2^v$ is as defined above;
or a pharmaceutically acceptable salt thereof, in nonsolvated form or a solvate thereof with a pharmaceutically acceptable solvent.

The most preferred values for such groups are: $R^{1v}$ is hydrogen; $R^{2v}$ is hydroxy, methoxy, ethoxy, phenoxyethyloxy,

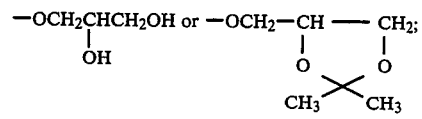

$W^v$ is hydroxy; $X^v$ is

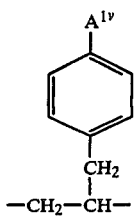

wherein $A^{1v}$ is as defined above; $Y^v$

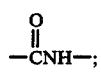

and $Z^v$ is p-phenylene or $-CH_2CHR^{4v}-$, wherein $R^{4v}$ is as defined above; Preferred compounds having the above structural formula are
N-[1-oxo-3-phenyl-2-(phosphonomethyl)propyl]-β-alanine and the ethyl ester thereof.

Examples of ACE inhibitors are those disclosed in the article by Wyvratt et al., cited above, and in the following patents and published patent applications:

U.S. Pat. No. 4,105,776 to Ondetti et al discloses proline derivatives which are angiotensin converting enzymes (ACE) inhibitors and have the general formula

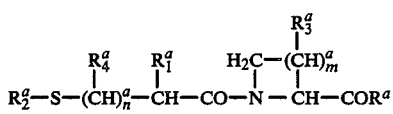

wherein
$R^a$ is hydroxy, $NH_2$ or lower alkoxy;
$R_1{}^a$ and $R_4{}^a$ each is hydrogen, lower alkyl, phenyl or phenyl-lower alkyl;
$R_2{}^a$ is hydrogen, lower alkyl, phenyl, substituted phenyl wherein the phenyl substituent is halo, lower alkyl or lower alkoxy, phenyl-lower alkyl, diphenyl-lower alkyl, triphenyl-lower alkyl, lower alkylthiomethyl, phenyl-lower alkylthiomethyl, lower alkanoyl-amidomethyl,

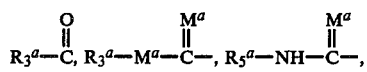

$R_4{}^a$—S—, or $R_6{}^a$
$R_3{}^a$ is hydrogen, hydroxy or lower alkyl;
$R_5{}^a$ is lower alkyl, phenyl or phenyl-lower alkyl;
$R_4{}^a$ is lower alkyl, phenyl, substituted phenyl (wherein the phenyl substituent is halo, lower alkyl or lower alkoxy), hydroxy-lower alkyl or amino(carboxy)-lower alkyl;

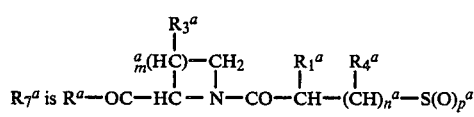

$M^a$ is O or S;
$m^a$ is 1 to 3;
$n^a$ and $p^a$ each is 0 to 2.

European Patent Application No. 97050 published Dec. 28, 1983 discloses phosphinylalkanoyl substituted prolines which have the formula

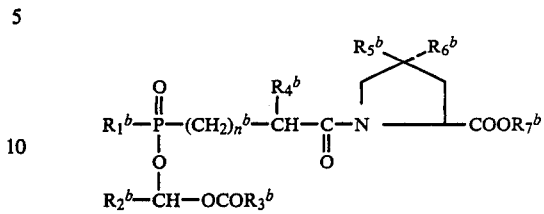

$R_1{}^b$ is alkyl, aryl, aralkyl, cycloalkyl or cycloalkylalkyl;
$R_2{}^b$ is cycloalkyl, 3-cyclohexenyl or 2-alkyl-3-cyclohexenyl;
$R_3{}^b$ is alkyl, cycloalkyl or phenyl;
$R_4{}^b$ is H or alkyl;
One of $R_5{}^b$ and $R_6{}^b$ is H and the other is alkyl—$X^b$—, phenyl—$X^b$—alkoxy, phenoxy, phenyl, cycloalkyl, alkyl or phenylalkyl; or
$R_5{}^b$ and $R_6{}^b$ together form $-X^bCH_2CH_2X^b-$, $X^b$ is S, SO or $SO_2$;
$R_7{}^b$ is H or $CH(R_2{}^b)OCOR_3{}^b$;
$n^b$ is 0 or 1;
'aryl' is phenyl opt. substituted by halo, alkyl, alkoxy, alkylthio, OH, alkanoyl, $NO_2$, amino, dialkylamino and/or $CF_3$; alkyl has 1-10C, cycloalkyl 3-7C, alkoxy 1-8C and alkanoyl 2-9C.

European Patent Application No. 83172 published July 6, 1983 discloses N-substituted acetyl-L-proline derivatives which are said to be angiotensin converting enzyme inhibitors and have the formula

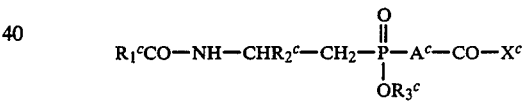

$R_1{}^c$ and $R_2{}^c$ are H, 1-7C alkyl, 1-7C haloalkyl, $(CH_2)_{m^c}$—$D^c$, 1-7C aminoalkyl or a group of formula:

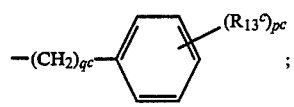

$D^c$ is cycloalkyl, furyl, thienyl or pyridinyl;
$A^c$ is $(CH_2)_n$—$CHR_{21}{}^c$, $NR_{22}{}^c$—$CHR_{23}{}^c$ or O—$CHR_{23}{}^c$;
$n^c$ is 0 or 1;
$g^c$ is 0–7;
$R_{21}{}^c$ is H, 1-7C alkyl, 1-7C haloalkyl, benzyl or phenethyl;
$R_{22}{}^c$ is H or 1-7C alkyl;
$R_{23}{}^c$ is H, 1-7C alkyl, 1-7C haloalkyl or $(CH_2)_{r^c}D_1{}^c$;
$D_1{}^c$ is phenyl, 4-hydroxyphenyl, 3,4-dihydroxyphenyl, 3-indolyl, 4-imidazolyl, $NH_2$, SH, 1-7C alkylthio, guanidino or $CONH_2$;
$X^c$ is a group of formula $(II)^c$-$(V)^c$, or $NR_4{}^c$—$CHR_5{}^c$—$COOR_6{}^c$;

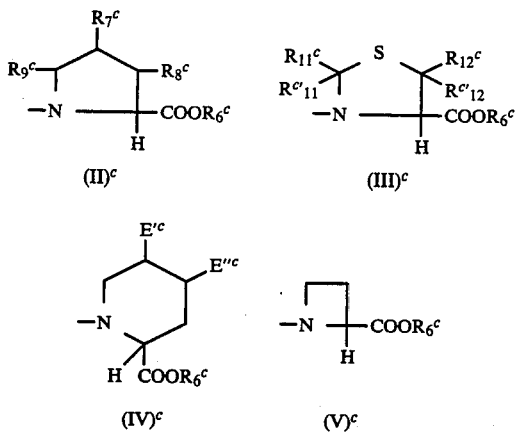

(II)$^c$ (III)$^c$ (IV)$^c$ (V)$^c$ where
$R_9{}^c$ and $R_8{}^c$ are H and $R_7{}^c$ is as defined below;
$R_9{}^c$ and $R_7{}^c$ are H and $R_8{}^c$ is as defined below;
$R_7{}^c$ and $R_8{}^c$ are H and $R_9{}^c$ is as defined below;
$R_9{}^c$ and $R_8{}^c$ are H and —CHR$_7{}^c$— is replaced by —CR$_{10}{}^c$R$_{10}{}^c$;
$R_9{}^c$ is H and $R_7{}^c + R_8{}^c$ form a double bond;
$R_9{}^c$ is H and $R_7{}^c + R_8{}^c$ complete a fused benzene ring; or
$R_8{}^c$ is H and $R_9{}^c + R_7{}^c$ complete a fused benzene ring;
$E'{}^c$ and $E''{}^c$ are H or $E'{}^c + E''{}^c$ complete a fused benzene ring;
$R_7{}^c$ is H, 1–7C alkyl, halogen, keto, OH, 2–8C alkanoyl-amino, $N_3$, $NH_2$, $NR_{19}{}^c R_{20}{}^c$, $(CH_2)_m{}^c$—$D^c$, O—CONR$_{15}{}^c$R$_{15}{}^c$, 1–7C alkoxy, 1–7C alkylthio, or a group of formula (VI)$^c$, (VII)$^c$ or (VIII)$^c$:

—NHCO—(CH$_2$)$_{mc}$—⟨ring⟩(R$_{14}{}^c$)$_{pc}$ (VI)$^c$

—B$'^c$—(CH$_2$)$_{mc}$—⟨ring⟩(R$_{13}{}^c$)$_{pc}$ (VII)$^c$

—B$'^c$—(CH$_2$)$_{mc}$—⟨naphthyl⟩(R$_{14}{}^c$)$_{pc}$ (VIII)$^c$ $B'^c$ is a bond or it is O or S; $R_8{}^c$ is keto, halogen, O—CONR$_{15}{}^c$R$_{15}{}^c$, 1–7C alkoxy 1–7C alkylthio, or a group (VII) or (VIII) in which
$B'^c$ is O or S;
$R_9{}^c$ is keto or a group (VII)$^c$ in which $B'^c$ is a bond;
$R_{10}{}^c$ is halogen or $Y^c R_{16}{}^c$;
$R_{11}{}^c$, $R'_{11}{}^c$, $R_{12}{}^c$ and $R'_{12}{}^c$ are H or 1–7C alkyl, or $R_{11}{}^c$ is a group of formula (IX)$^c$ and the other 3 are H;

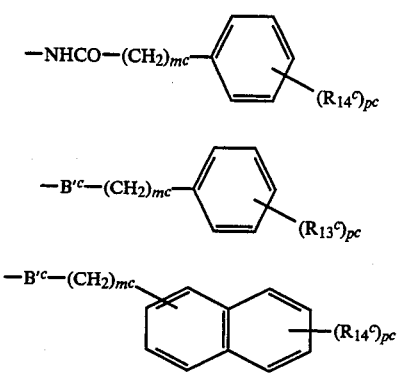

(IX)$^c$ $R_{13}{}^c$ is H, 1–4C alkyl, 1–4C alkoxy, 1–4C alkylthio, Cl, Br, F, CF$_3$, OH, Ph, PhO, PhS or PhCH$_2$;
$R_{14}{}^c$ is H, 1–4C alkyl, 1–4C alkoxy, 1–4C alkylthio, Cl, Br, F, CF$_3$ or OH;
$m^c$ is 0–3;
$p^c$ is 1–3 but it is 2 or 3 only when $R_{13}{}^c$ or $R_{14}{}^c$ is H, Me, MeO, Cl or F;
$R_{15}{}^c$ is H or 1–4C alkyl;
$Y^c$ is O or S;
$R_{16}{}^c$ is 1–4C alkyl or group (VII)$^c$ in which $B'^c$ is a bond; or the two $R_{16}{}^c$ groups complete a 5- or 6-membered ring in which the C atoms may each bear 1 or 2 alkyls having 1–4 C
$R_4{}^c$ is H, 1–7C alkyl, cycloalkyl or (CH$_2$)$_r{}^c$Ph;
$R_5{}^c$ is H, 1–7C alkyl or (CH$_2$)$_r{}^c$—D$_1{}^c$;
$r^c$ is 1–4;
$R_3{}^c$ and $R_6{}^c$ are H, 1–7C alkyl, PhCH$_2$, PhCH or CHR$_{17}{}^c$—O—COR$_{18}{}^c$;
$R_{17}{}^c$ is H, 1–7C alkyl or Ph;
$R_{18}{}^c$ is H, 1–7C alkyl, 1–7C alkoxy or Ph; or
$R_{17}{}^c + R_{18}{}^c$ form (CH$_2$)$_2$, (CH$_2$)$_3$, —CH=CH or o-phenylene;
$R_{19}{}^c$ is 1–7C alkyl, benzyl or phenethyl; and
$R_{20}{}^c$ is H or chosen as for $R_{19}{}^c$.

European Patent Application No. 0 012 401 published June 25, 1980 discloses carboxyalkyl dipeptide derivatives which are said to be angiotensin converting enzyme inhibitors and have the formula $$R^d-\overset{O}{\underset{}{C}}-\overset{R^{1d}}{\underset{R^{2d}}{C}}-NH-\overset{R^{3d}}{\underset{}{CH}}-\overset{}{\underset{O}{C}}-\overset{R^{4d}}{\underset{R^{7d}}{N}}-\overset{R^{5d}}{\underset{}{C}}-\overset{O}{\underset{}{C}}-R^{6d} \quad I$$

wherein
$R^d$ and $R^{6d}$ are the same or different and are hydroxy, lower alkoxy, lower alkenoxy, dilower alkylamino lower alkoxy (dimethylaminoethoxy), acylamino lower alkoxy (acetylaminoethoxy), acyloxy lower alkoxy (pivaloyloxymethoxy), aryloxy, such as phenoxy, arloweralkoxy, such as benxyloxy, substituted aryloxy or substituted arloweralkoxy wherein the substituent is methyl, halo or methoxy, amino, loweralkylamino, diloweralkylamino, hydroxyamino, arloweralkylamino such as benzylamino;
$R^{1d}$ is hydrogen, alkyl of from 1 to 20 carbon atoms which include branched and cyclic and unsaturated (such as allyl) alkyl groups, substituted loweralkyl wherein the substituent can be halo, hydroxy, lower alkoxy, aryloxy such as phenoxy, amino, diloweralkylamino, acylamino, such as acetamido and benzamido, arylamino, guanidino, imidazolyl, indolyl, mercapto, loweralkylthio, arylthio such as phenylthio, carboxy or carboxamido, carboloweralkoxy, aryl such as phenyl or naphthyl, substituted aryl such as phenyl wherein the substituent is lower alkyl, lower alkoxy or halo, arloweralkyl, arloweralkenyl, heteroarlower alkyl or heteroarlower alkenyl such as benzyl, styryl or indolyl ethyl, substituted arloweralkyl, substituted arloweralkenyl, substituted heteroarlower alkyl, or substituted heteroarlower alkenyl, wherein the substituent(s) is halo, dihalo, lower alkyl, hydroxy, lower alkoxy, amino, aminomethyl, acylamino (acetylamino or benzoylamino) diloweralkylamino, loweralkylamino, carboxyl, haloloweralkyl, cyano or sulfonamido; arloweralkyl or heteroarloweralkyl substituted on the alkyl portion by amino or acylamino (acetylamino or benzoylamino);

$R^{2d}$ and $R^{7d}$ are the same or different and are hydrogen or lower alkyl;

$R^{3d}$ is hydrogen, lower alkyl, phenyl lower alkyl, aminomethyl phenyl lower alkyl, hydroxy phenyl lower alkyl, hydroxy lower alkyl, acylamino lower alkyl (such as benzoylamino lower alkyl, acetylamino lower alkyl), amino lower alkyl, dimethylamino lower alkyl, halo lower alkyl, guanidino lower alkyl, imidazolyl lower alkyl, indolyl lower alkyl, mercapto lower alkyl, lower alkyl thio lower alkyl;

$R^{4d}$ is hydrogen or lower alkyl;

$R^{5d}$ is hydrogen, lower alkyl, phenyl, phenyl lower alkyl, hydroxy phenyl lower alkyl, hydroxy lower alkyl, amino lower alkyl, guanidino lower alkyl, imidazolyl lower alkyl, indolyl lower alkyl, mercapto lower alkyl or lower alkylthio lower alkyl;

$R^{4d}$ and $R^{5d}$ may be connected together to form an alkylene bridge of from 2 to 4 carbon atoms, an alkylene bridge of from 2 to 3 carbon atoms and one sulfur atom, an alkylene bridge of from 3 to 4 carbon atoms containing a double bond or an alkylene bridge as above substituted with hydroxy, loweralkoxy, lower alkyl or di-lower alkyl;

and the pharmaceutically acceptable salts thereof.

U.S. Pat. No. 4,462,943 to Petrillo et al discloses carboxyalkyl amino acid derivatives of substituted prolines which are angiotensin converting enzyme inhibitors and have the formula

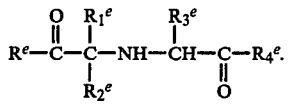

$R_4^e$ is a substituted proline of the formula

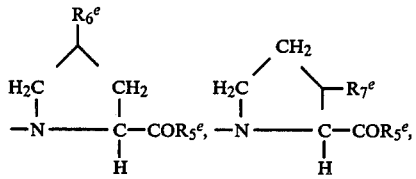

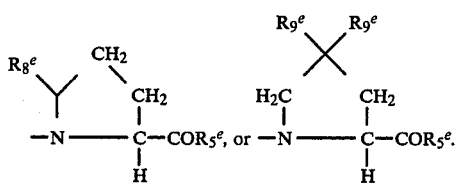

$R_6^e$ is halogen, keto, azido,

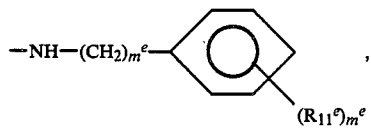

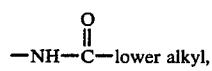

—NH—C—lower alkyl,

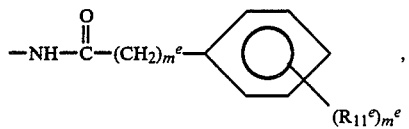

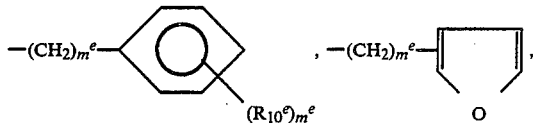

a 1- or 2-naphthyl of the formula

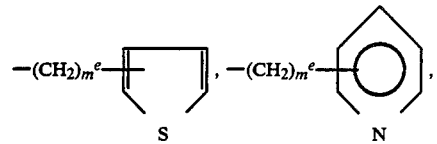

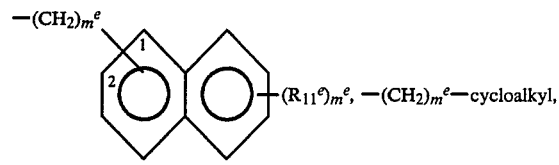

a 1- or 2-naphthyloxy of the formula

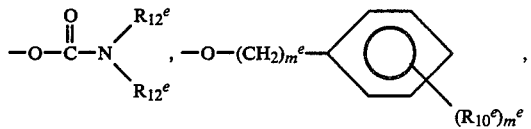

—S—lower alkyl,

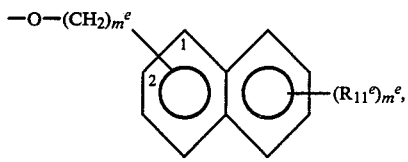

or a 1- or 2-naphthylthio of the formula

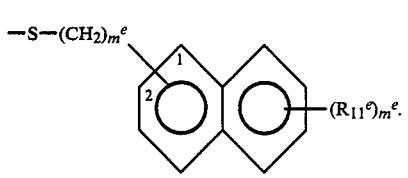

$R_7^e$ is keto, halogen,

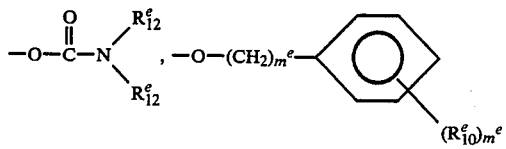

a 1- or 2-naphthloxy of the formula

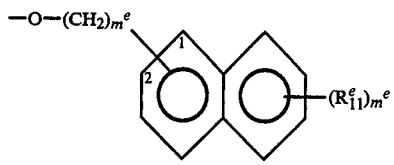

—S-lower alkyl,

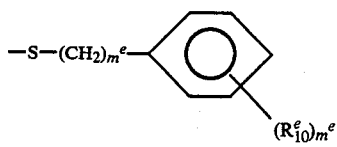

or a 1- or 2-naphthylthio of the formula or a 1- or 2-naphthylthio of the formula

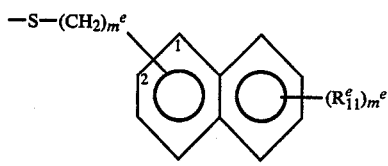

$R_8^e$ is keto or

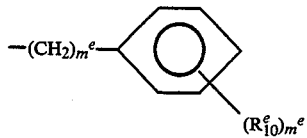

$R_9^e$ is halogen or —$Y^e$—$R_{13}^e$.

$m^e$ is zero, one, two, or three.

$R_{10}^e$ is hydrogen, lower alkyl of 1 to 4 carbons, lower alkoxy of 1 to 4 carbons, lower alkylthio of 1 to 4 carbons, chloro, bromo, fluor, trifluoromethyl, hydroxy, phenyl, phenoxy, phenylthio, or phenylmethyl.

$R_{11}^e$ is hydrogen, lower alkyl of 1 to 4 carbons, lower alkoxy of 1 to 4 carbons, lower alkylthio of 1 to 4 carbons, bromo, fluoro, trifluoromethyl, or hydroxy.

$n^e$ is one, two or three provided that $n^e$ is more than one only if $R_{10}^e$ is hydrogen, methyl, methoxy, chloro, or fluoro.

$R_{12}^e$ is hydrogen or lower alkyl of 1 to 4 carbons.

$Y^e$ is oxygen or sulfur.

$R_{13}^e$ is lower alkyl of 1 to 4 carbons.

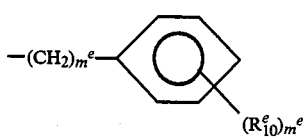

or the $R_{13}^e$ group join to complete an unsubstituted 5- or 6-membered ring or said ring in which one or more of the carbons has a lower alkyl of 1 to 4 carbons, or a di(lower alkyl of 1 to 4 carbons) substituent.

$R^e$ and $R_5^e$ are independently selected from hydroxy, lower alkoxy, di(lower alkyl)-amino-lower alkoxy, such as dimethylaminoethoxy, lower alkyl-carbonyl-amino-lower alkoxy, such as acetylaminoethoxy, lower alkyl-carbonyloxy-lower alkoxy, such as pivaloyloxymethoxy.

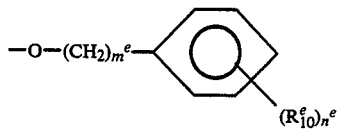

wherein $m^e$, $n^e$ and $R_{10}^e$ are as defined above, amino, lower alkyl-amino, di(lower alkyl)-amino, hydroxyamino, benzylamino, or phenethylamino.

$R_1^e$ is hydrogen, lower alkyl.

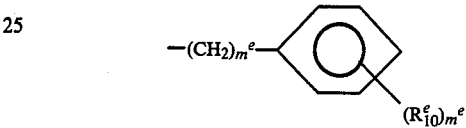

halo substituted lower alkyl, hydroxy substituted lower alky, —$(CH_2)_q^e$—cycloalkyl, —$(CH_2)_q^e$—carboxy, —$(CH_2)_q^e$—S-lower alkyl,

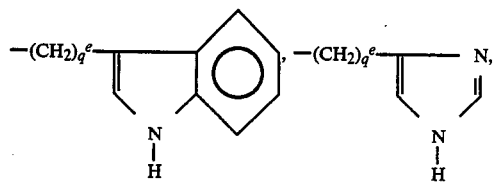

—$(CH_2)_q^e$—guanidinyl, —$(CH_2)_q^e$—$NH_2$,

—$(CH_2)_q^e$—N(lower alkyl)$_2$,

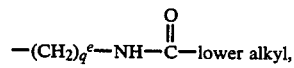

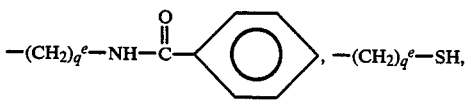

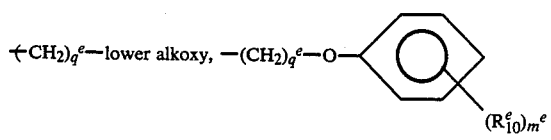

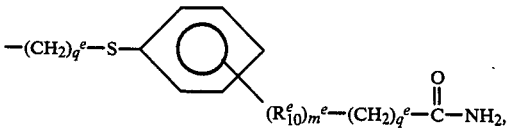

-continued

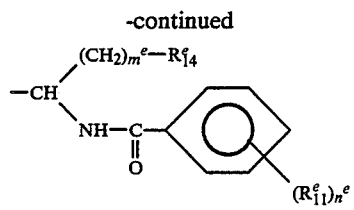

wherein $m^e$, $n^e$, $R_{10}^e$ and $R_{11}^e$ are as defined above, $R_{14}^e$ is lower alkyl, cycloalkyl, or and $q^e$ is

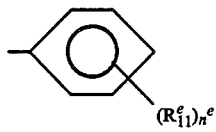

an integer from 1 to 4.

$R_2^e$ is hydrogen or lower alkyl.

$R_3^e$ is hydrogen, lower alkyl, halo substituted lower alkyl, hydroxy substituted lower alkyl, —(CH$_2$)$_q^e$—NH$_2$, —(CH$_2$)$_q^e$13 N-(lower alkyl)$_2$, —(CH$_2$)$_q^e$ guanidinyl, —(CH$_2$)$_q^e$—SH, —(CH$_2$)$_q^e$—S-lower alkyl,

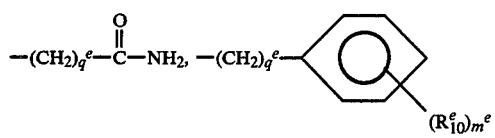

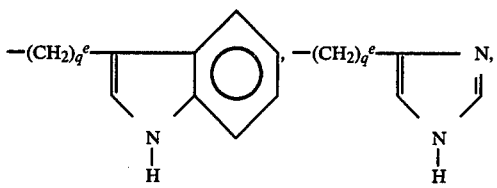

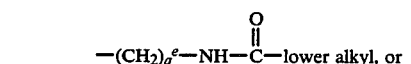

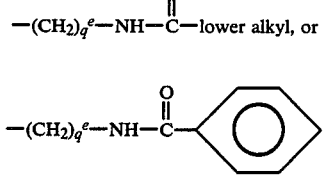

wherein $R_{10}^e$, $n^e$ and $q^e$ are as defined above.

U.S. Pat. No. 4,470,973 to Natarajan et al discloses substituted peptides which are angiotensin converting enzymes inhibitors and have the formula

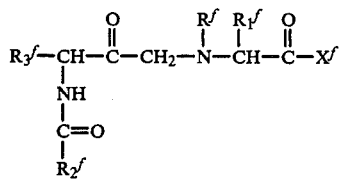

$X^f$ is an amino or imino acid of the formula

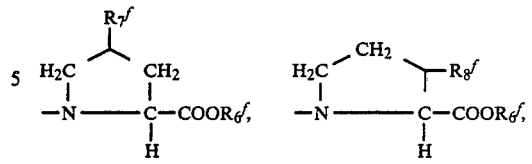

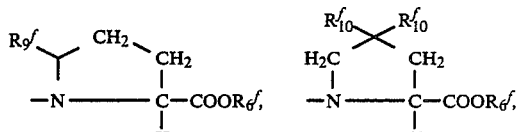

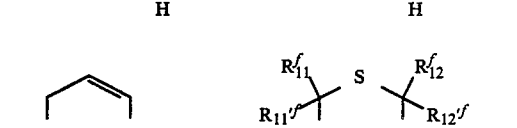

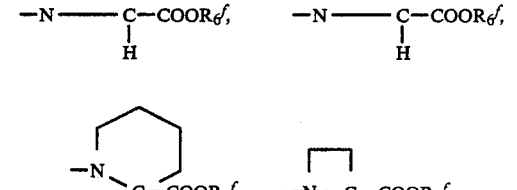

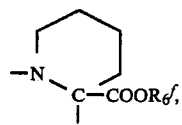

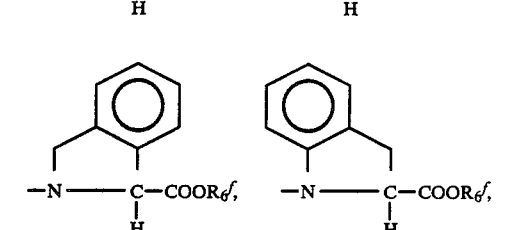

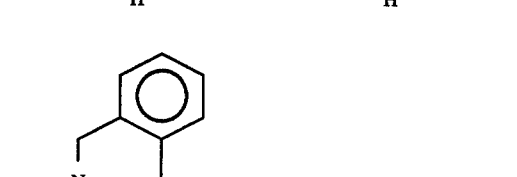

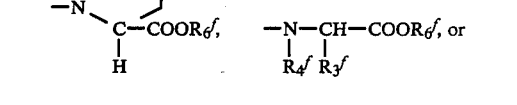

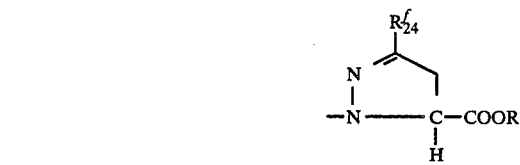

$R_7^f$ is hydrogen, lower alkyl, halogen, keto, hydroxy,

—NH—C(=O)—lower alkyl, azido, amino,

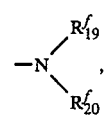

-continued

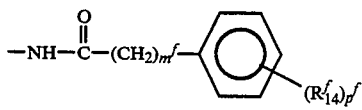

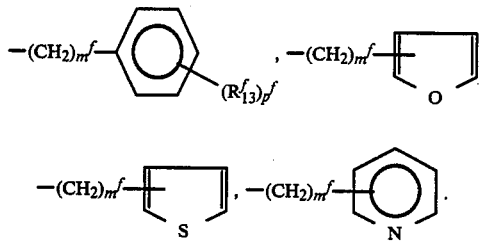

a 1- or 2-naphthyl of the formula

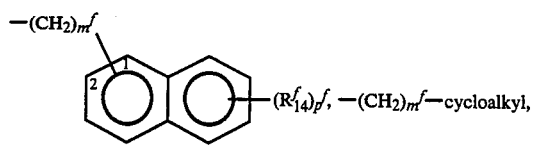

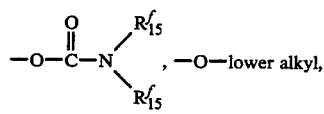

a 1- or 2-naphthyloxy of the formula

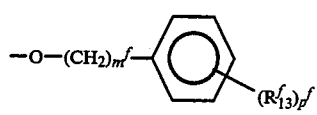

—S—lower alkyl,

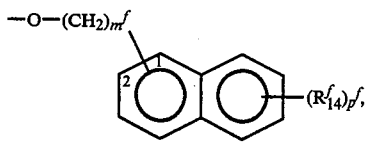

or a 1- or 2-naphthylthio of the formula

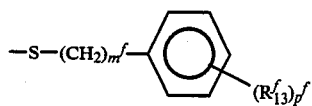

$R_8{}^f$ is keto, halogen,

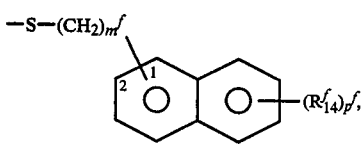

-continued

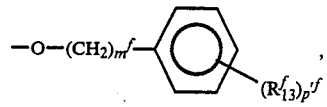

—O—lower alkyl, a 1- or 2-naphthyloxy of the formula

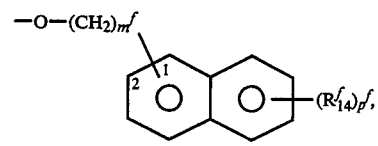

—S—lower alkyl,

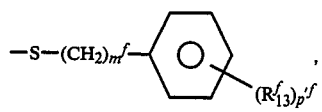

or a 1- or 2-naphthylthio of the formula

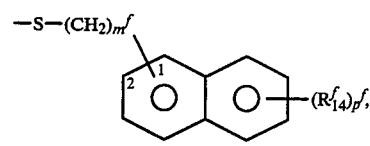

$R_9{}^f$ is keto or

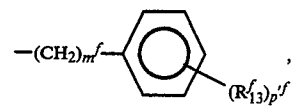

$R_{10}{}^f$ is halogen or $-Y^f-R_{16}{}^f$.

$R_{11}{}^f$, $R_{11'}{}^f$, $R_{12}{}^f$ and $R_{12'}{}^f$ are independently selected from hydrogen and lower alkyl or $R_{11'}{}^f$, $R_{12}{}^f$ and $R_{12'}{}^f$ are hydrogen and $R_{11}{}^f$ is

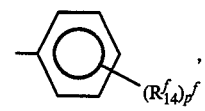

$R_{13}{}^f$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl.

$R_{14}{}^f$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy.

$m^f$ is zero, one, two, three, or four.

$p^f$ *is one, two or three provided that p is more than one only if $R_{13}{}^f$ or $R_{14}{}^f$ is hydrogen, methyl, methoxy, chloro, or fluoro.*

$R_{15}{}^f$ is hydrogen or lower alkyl of 1 to 4 carbons.

$Y^f$ is oxygen or sulfur.

$R_{16}{}^f$ is lower alkyl of 1 to 4 carbons,

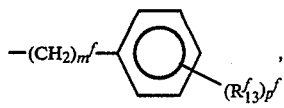, or the $R_{16}{}^f$ groups join to complete an unsubstituted 5- or 6-membered ring or said ring in which one or more of the carbons has a lower alkyl of 1 to 4 carbons or a di(lower alkyl of 1 to 4 carbons) substituent.

$R_4{}^f$ is hydrogen, lower alkyl,

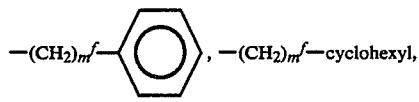

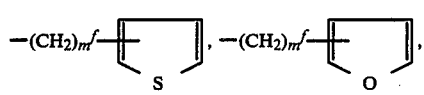

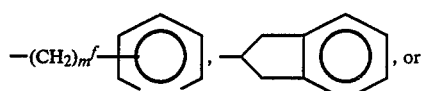

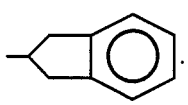

$R_5{}^f$ a hydrogen, lower alkyl,

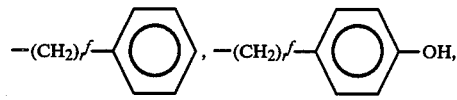

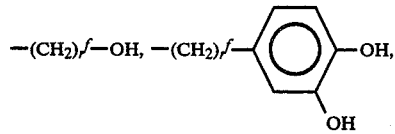

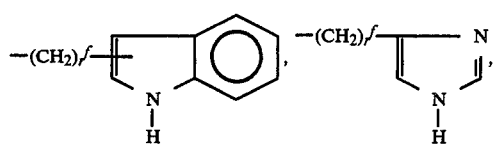

—(CH$_2$)$_{r'}$—NH$_2$, —(CH$_2$)$_{r'}$—SH, —(CH$_2$)$_{r'}$—S—lower alkyl,

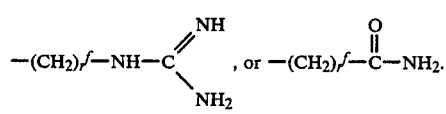

$r^f$ is an integer from 1 to 4.
$R_{19}{}^f$ is lower alkyl, benzyl, or phenethyl.
$R_{20}{}^f$ is hydrogen, lower alkyl, benzyl or phenethyl.
$R^f$ is hydrogen, lower alkyl, cycloalkyl,

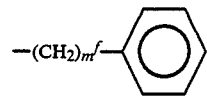

—(CH$_2$)$_2$—NH$_2$, —(CH$_2$)$_3$—NH$_2$, —(CH$_2$)$_4$—NH$_2$,
—(CH$_2$)$_2$—OH, —(CH$_2$)$_3$—OH, —(CH$_2$)$_4$—OH,
—(CH$_2$)$_2$—SH, —(CH$_2$)$_3$—SH, or —(CH$_2$)$_4$—SH.

$R_1{}^f$ is hydrogen, lower alkyl, halo substituted lower alkyl,

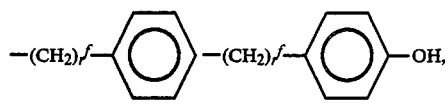

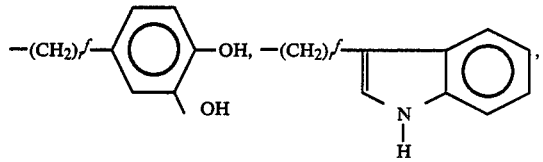

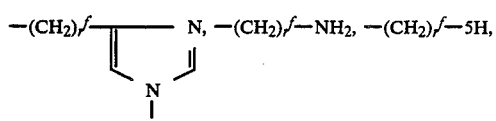

—(CH$_2$)$_{r'}$—OH, —(CH$_2$)$_{r'}$—S—lower alkyl,

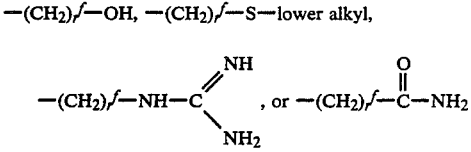

provided that $R_1{}^f$ is hydrogen only if $R^f$ is other than hydrogen.

$R_2{}^f$ is

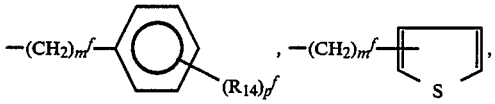

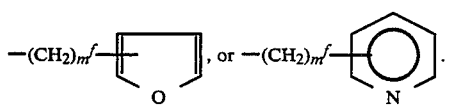

$R_3{}^f$ is hydrogen, lower alkyl,

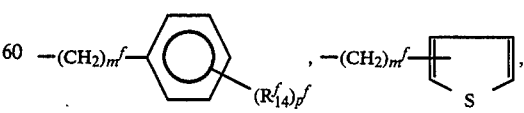

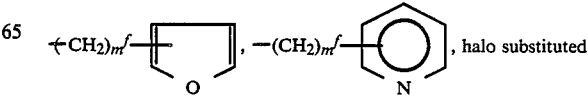

-continued lower alkyl, $-(CH_2)_{m'}-$cycloalkyl, $-(CH_2)_{r'}-$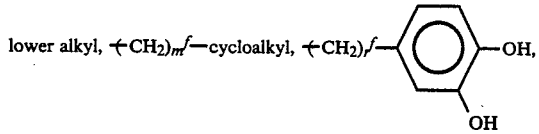

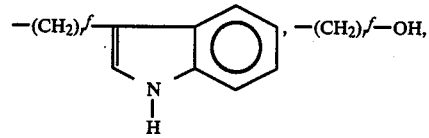

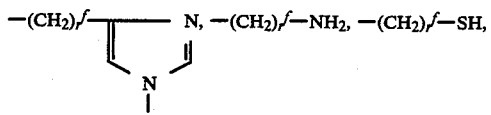

$-(CH_2)_{r'}-S-$lower alkyl, $-(CH_2)_{r'}-NH-C\begin{smallmatrix}NH\\\|\\NH_2\end{smallmatrix}$ or

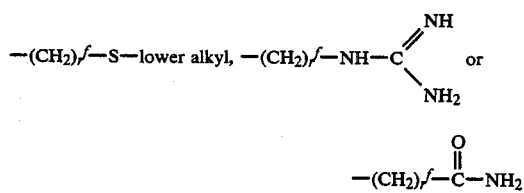

wherein $m'$, $R_{14}'$, $p'$ and $r'$ are as defined above.

$R_6'$ is hydrogen, lower alkyl, benzyl, benzhydryl,

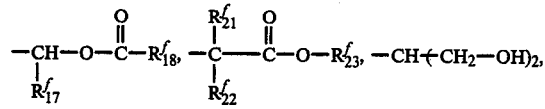

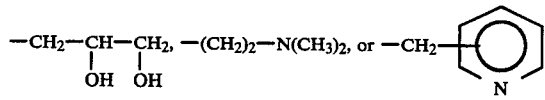

$R_{17}'$ is hydrogen, lower alkyl, cycloalkyl, or phenyl.
$R_{18}'$ is hydrogen, lower alkyl, lower alkoxy, or phenyl or $R_{17}'$ and $R_{18}'$ taken together are $-(CH_2)_2-$, $-(CH_2)_3-$, $-CH=CH-$, or

$R_{21}'$ and $R_{22}'$ are independently selected from hydrogen and lower alkyl.
$R_{23}'$ is lower alkyl.
$R_{24}'$ is hydrogen, lower alkyl,

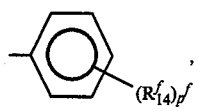

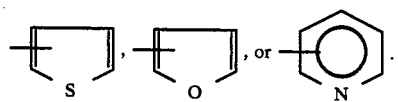

British Specification No. 2095682 published Oct. 6 1982 discloses N-substituted-N-carboxyalkyl aminocarbonyl alkyl glycine derivatives which are said to be angiotensin converting enzyme inhibitors and have the formula

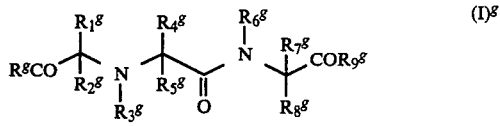

either (A) $R^g$ and $R_9^g$ are OH, 1-6C alkoxy, 2-6C alkenyloxy, di-(1-6C alkyl)amino-(1-6C) alkoxy, 1-6C hydroxyalkoxy, acylamino-(1-6C)alkoxy, acyloxy-(1-6C)alkoxy, aryloxy, aryloxy-(1-6C)alkoxy, NH$_2$, mono- or di-(1-6C) alkyl)amino, hydroxyamino or aryl-(1-6C)alkylamino;

$R_1^g$-$R_5^g$, $R_7^g$ and $R_8^g$ are 1-20C alkyl, 2-20C alkenyl, 2-20C alkynyl, aryl, aryl-(1-6C) alkyl having 7-12C or heterocyclyl-(1-6C)alkyl having 7-12C;

$R_6^g$ is cycloalkyl, polycycloalkyl, partly saturated cycloalkyl or polycycloalkyl, cycloalkyl-(1-6C)alkyl having 3-20C, 6-10C aryl, aryl-(1-6C)alkyl, aryl-(2-6C)alkenyl or aryl-(2-6C) alkynyl; or $R_2^g$ and $R_3^g$ together with the C and N atoms to which they are attached or $R_3^g$ and $R_5^g$ together with the N and C atoms to which they are attached form an N-heterocycle containing 3-5C or 2-4C and a S atom;

all alkyl, alkenyl and alkynyl are optionally substituted by OH, 1-6C alkoxy, thio(sic), 1-6C alkylthio, NH$_2$, mono— or di(1-6C alkyl)amino, halogen or NO$_2$;

all 'cycloalkyl' groups (including poly and partially unsaturated) are optionally substituted by halogen, 1-6C hydroxyalkyl, 1-6C alkoxy, amino-(1-6C alkyl)amino, di-(1-6C alkyl)amino, SH, 1-6C alkylthio, NO$_2$ or CF$_3$; and aryl groups are optionally substituted by OH, 1-6C alkoxy, NH$_2$, mono— or di-(1-6C alkyl) amino, SH, 1-6C alkylthio, 1-6C hydroxyalkyl, 1-6C aminoalkyl, 1-6C thioalkyl, NO$_2$, halogen, CF$_3$, OCH$_2$O, ureido or guanidino; or (B) $R^g$ and $R_9^g$ are H or 1-6C alkoxy; $R_1^g$ and $R_2^g$ are H, 1-6C alkyl, aryl-(1-6C) alkyl having 7-12C or heterocyclyl-(1-6C) alkyl having 6-12C;

$R_3^g$-$R_5^g$, $R_7^g$ and $R_8^g$ are H or 1-6C alkyl;

$R_6^g$ is cycloalkyl, polycycloalkyl partly saturated cycloalkyl or polycycloalkyl, cycloalkyl-(1-6C) alkyl having 3-20C, aryl or aryl-(1-6C) alkyl; and aryl has 6-10C and is optionally substituted by 1-6C alkyl, 2-6C alkenyl, 2-6C alkynyl, OH, 1-6C alkoxy, NH$_2$, mono— or di-(1-6C alkyl) amino, SH, 1-6C alkylthio, 1-6C hydroxyalkyl, 1-6C aminoalkyl, 1-6C thioalkyl, NO$_2$, halogen, CF$_3$, OCH$_2$O, ureido or guanidino.

U.S. Pat. No. 4,470,972 to Gold et al discloses 7-carboxyalkyl-aminoacyl-1,4-dithia-7-azaspiro[4.4]nonane-8-carboxylic acids which are angiotensin converting enzyme inhibitors and have the formula

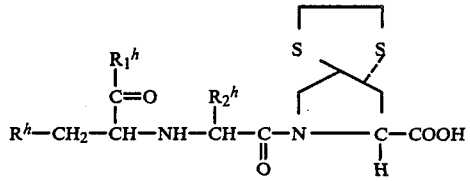

wherein $R^h$ is lower alkyl, benzyl, benzylthio, benzyloxy, phenylthio or phenoxy;

$R_1^h$ is hydroxy or lower alkoxy;

$R_2^h$ is hydrogen, lower alkyl or amino lower alkyl; and the pharmaceutcally acceptable salts thereof.

European Patent Application No. 0 050 800 published May 5, 1982 discloses carboxyalkyl dipeptides derivatives which are said to be angiotensin converting enzyme inhibitors and have the formula

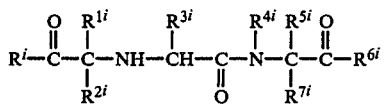

or a pharmaceutically acceptable salt thereof, wherein $R^i$ and $R^{6i}$ are the same or different and are hydroxy, lower alkoxy, lower alkenyloxy, dilower alkylamino lower alkoxy, acylamino lower alkoxy, acyloxy lower alkoxy, aryloxy, aryllower alkoxy, amino, lower alkylamino, dilower alkylamino, hydroxyamino, aryllower alkylamino, or substituted aryloxy or substituted aryllower alkoxy wherein the substitutent is methyl, halo or methoxy; $R^{1i}$ is hydrogen, alkyl of from 1 to 10 carbon atoms, substituted lower alkyl wherein the substitutent is hydroxy, lower alkoxy, aryloxy, substituted aryloxy, heteroaryloxy, substituted heteroaryloxy, amino, lower alkylamino, diloweralkylamino, acylamino, arylamino, substituted arylamino, guanidino, imidazolyl, indolyl, lower alkylthio, arylthio, substituted arylthio, carboxy, carbamoyl, lower alkoxy carbonyl, aryl, substituted aryl, aralkyloxy, substituted aralkyloxy, aralkylthio or substituted aralkylthio, wherein the aryl or heteroaryl portion of said substituted aryloxy, heteroaryloxy, arylamino, arylthio, aryl, aralkyloxy, aralkylthio group is substituted with a group selected from halo, lower alkyl, hydroxy, lower alkoxy, amino, aminomethyl, carboxyl, cyano, or sulfamoyl; $R^{2i}$ and $R^{7i}$ are the same or different and are hydrogen or lower alkyl; $R^{3i}$ is hydrogen, lower alkyl, phenyl lower alkyl, aminomethylphenyl lower alkyl, hydroxyphenyl lower alkyl, hydroxy lower alkyl, acylamino lower alkyl, amino lower alkyl, dimethylamino lower alkyl, guanidino lower alkyl, imidazolyl lower alkyl, indolyl lower alkyl, or lower alkyl thio lower alkyl; $R^{4i}$ and $R^{5i}$ are the same or different and are hydrogen, lower alkyl or $Z^i$, or $R^{4i}$ and $R^{5i}$ taken together form a group represented by $C^i$, $U^i$, $V^i$, $Y^i$, $D^i$ or $E^i$, wherein;

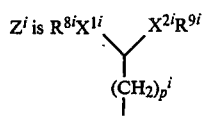

wherein $X^{1i}$ and $X^{2i}$ independent of each other are O, S or $CH_2$, $R^{8i}$ and $R^{9i}$ independent of each other are lower alkyl, lower alkenyl, lower alkynyl, cycloalkyl having 3 to 8 carbon atoms, hydroxy lower alkyl, or $-(CH_2)_{n^i}Ar^i$, wherein $n^i$ is 0, 1, 2 or 3 and $Ar^i$ is unsubstituted or substituted phenyl, furyl, thienyl or pyridyl, wherein said substituted phenyl, furyl, thienyl or pyridyl groups are substituted with at least one group that is independently selected from $C_1$ to $C_4$ alkyl, lower alkoxy, lower alkylthio, halo, $CF_3$ and hydroxy, or $R^{8i}$ and $R^{9i}$ taken together form a bridge $W^i$, wherein $W^i$ is a single bond or a methylene bridge or a substituted methylene bridge when at least one of $X^{1i}$ and $X^{2i}$ is methylene, or $W^i$ is an alkylene or substituted alkylene bridge having 2 or 3 carbon atoms, said substituted methylene bridge or said substituted alkylene bridge having one or two substituents selected from lower alkyl, aryl and aryl lower alkyl groups, and $p^i$ is 0, 1 or 2; with the proviso that at least one of $R^{4i}$ and $R^{5i}$ is $Z^i$, with the proviso that if $R^{4i}$ is $Z^i$ and $p^i$ is 0 then $X^{1i}$ and $X^{2i}$ must both be methylene, and with the proviso that if $X^{1i}$ and $X^{2i}$ are both methylene then $R^{8i}$ and $R^{9i}$ must form an alkylene bridge $W^i$;

$Q^i$ is

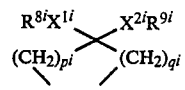

wherein $R^{8i}$, $R^{9i}$, $X^{1i}$ and $X^{2i}$ are as defined above, $p^i$ is 0, 1 or 2, $q^i$ is 0, 1 or 2, with the proviso that the sum of $p^i$ and $q^i$ must be 1, 2 or 3, with the proviso that if $p^i$ is 0 then $X^{1i}$ and $X^{2i}$ must be methylene, and with the proviso that if $X^{1i}$ and $X^{2i}$ are methylene then $R^{8i}$ and $R^{9i}$ taken together form a bridge $W^i$, wheren $W^i$ is as defined above;

$V^i$ is

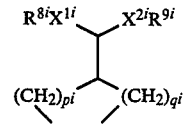

wherein $R^{8i}$, $R^{9i}$, $X^{1i}$ $X^{2i}$ are as defined above, $p^i$ is 0, 1 or 2 and $q^i$ is 0, 1 or 2, with the proviso that the sum of $p^i$ and $q^i$ is 1, 2 or 3, with the proviso that if $X^{1i}$ and $X^{2i}$ are $CH_2$ then $R^{8i}$ and $R^{9i}$ taken together form a bridge $W^i$, wherein $W^i$ is as defined above;

$U^i$ is

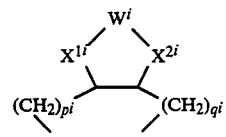

wherein $W^i$ is as defined above (except that $W^i$ may also be a methylene bridge when $X^{1i}$ and $X^{2i}$ are oxygen or sulfur), $X^{1i}$ and $X^{2i}$ are as defined above, $p^i$ is 0, 1 or 2, $q^i$ is 0, 1 or 2, with the proviso that the sum of $p^i$ and $q^i$ is 1 or 2, and with the proviso that if $p^i$ is 0, $X^{1i}$ must be $CH_2$;

$Y^i$ is

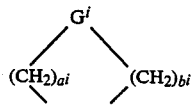

wherein $G^i$ is oxygen, sulfur or $CH_2$, $a^i$ is 2, 3 or 4 and $b$ is 1, 2, 3, 4 or 5, with the proviso that the sum of $a^i$ and $b^i$ is 5, 6 or 7 or $G^i$ is $CH_2$, $a^i$ is 0, 1, 2 or 3, $b^i$ is 0, 1, 2 or 3 with the proviso that the sum of $a^i$ and $b^i$ is 1, 2 or 3, with the proviso that the sum of $a^i$ and $b^i$ may be 1, 2 or 3 only if $R^{1i}$ is lower alkyl substituted with aralkylthio or aralkyloxy;
$D^i$ is

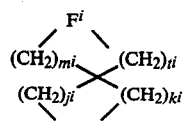

wherein $F^i$ is O or S, $j^i$ is 0, 1 or 2 and $k^i$ is 0, 1 or 2, with the proviso that the sum of $j^i$ and $k^i$ must be 1, 2 or 3, and $m^i$ is 1, 2 or 3 and $t^i$ is 1, 2 or 3, with the proviso that the sum of $m^i$ and $t^i$ must be 2, 3 or 4;
$E^i$ is

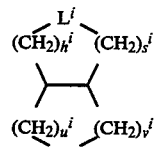

wherein $L^i$ is O or S, $u^i$ is 0, 1 or 2 and $V^i$ is 0, 1 or 2, with the proviso that the sum of $u^i$ and $v^i$ must be 1 or 2, and $h^i$ is 1 or 2 and $s^i$ is 1 or 2, with the proviso that the sum of $h^i$ and $s^i$ must be 2 or 3.

European Patent Application No. 0 037 231 published Oct. 7, 1981 discloses acyl derivatives of octahydro-1H-indole-2-carboxylic acids which are said to be angiotensin converting enzyme inhibitors and have the formula

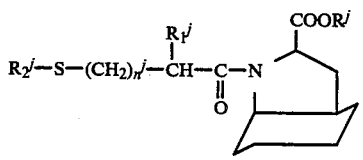

wherein $R^j$ is hydrogen or lower alkyl; $R_1{}^j$ is hydrogen, lower alkyl, or benzyl; $R_2{}^j$ is hydrogen or

wherein $R_3{}^j$ is lower alkyl, heteroaryl containing 4 to 9 carbon atoms and one or two nitrogen, oxygen or sulfur atoms; phenyl, substituted phenyl having 1 or 2 substituents selected from the group consisting of fluorine, chlorine, bromine, lower alkyl or alkoxy; and n is 0 or 1; wherein lower alkyl and lower alkoxy include straight or branched groups containing 1 to 4 carbon atoms, and pharmaceutically acceptable salts of the compounds when $R^j$ is hydrogen and when $R_3{}^j$ is heteroaryl containing 1 or 2 nitrogen atoms. Also disclosed are substituted acyl compounds of octahydro-1H-indole-2-carboxylic acid having the formula

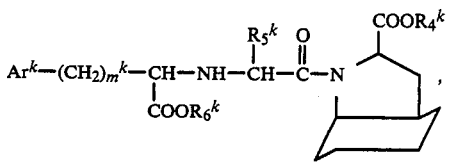

wherein $R_4{}^k$ is hydrogen or lower alkyl; $R_5{}^k$ is hydrogen, lower alkyl or benzyl; $R_6{}^k$ is hydrogen or lower alkyl; $Ar^k$ is phenyl or phenyl substituted with 1 or 2 substituents selected from the group consisting of fluorine, chlorine, bromine, lower alkyl, lower alkoxy, hydroxy or amino; and m is 0 to 3; wherein lower alkyl and lower alkoxy contain 1 to 4 straight or branched carbon atoms; and the pharmaceutically acceptable salts thereof.

European Patent Application No. 0 079 522 published May 25, 1983 discloses N-carboxymethyl(amino)lysl-proline compounds which are said to be angiotensin converting enzyme inhibitors and have the formula where

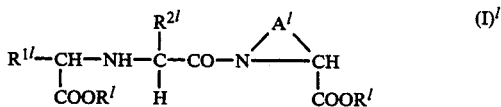

and

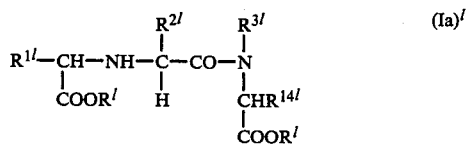

wherein:
$R^l$ and $R^{2l}$ are independently hydrogen; loweralkyl; aralkyl; or aryl;
$R^{1l}$ is hydrogen; branched or straight chain $C_{1-12}$ alkyl and alkenyl; $C_3-C_9$ cycloalkyl and benzofused alkyl; substituted loweralkyl where the substituents are halo, hydroxy loweralkoxy, aryloxy, amino, mono- or diloweralkylamino, acylamino, arylamino, guanidino, mercapto, loweralkylthio, arylthio, carboxy, carboxamido, or loweralkoxycarbonyl; aryl; substituted aryl where the substituents are loweralkyl, loweralkoxy, or halo; arloweralkyl; arloweralkenyl; heteroarloweralkyl; heteroarloweralkenyl; substituted arloweralkyl, substituted arloweralkenyl, substituted heteroarloweralkyl, or substituted heteroarloweralkenyl where the aryl and heteroaryl substituents are halo, dihalo, loweralkyl, hydroxy, loweralkoxy, amino, aminoloweralkyl, acrylamino, mono- or diloweralkylamino, carboxyl, haloloweralkyl, nitro, cyano, or sulfonamido, and where the loweralkyl portion of arloweralkyl may be substituted by amino, acylamino, or hydroxyl;

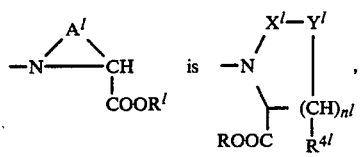

is

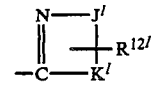

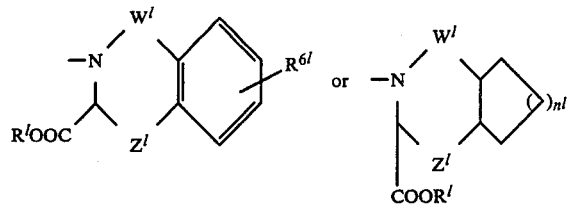

where
$X^l$ and $Y^l$ taken together are —CH$_2$—CH$_2$—;

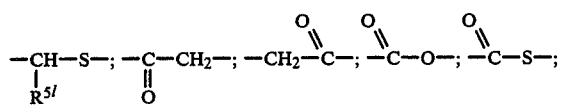

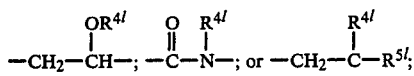

$R^{4l}$ is hydrogen; loweralkyl; aryl; substituted aryl;
$R^{5l}$ is hydrogen; loweralkyl; aryl or substituted aryl;
$n^l$ is 1 or 3;
$W^l$ is absent; —CH$_2$—; or

$Z^l$ is $-(CH_2)_{m^l}-$, where m is 0 to 2, provided that $m^l$ may not be 0 and $W^l$ may not be absent at the same time; and
$R^{6l}$ is hydrogen; loweralkyl; halo; or $OR^{4l}$;

$R^{2l}$ is $-(CH_2)_{r^l}B^l-(CH_2)_{s^l}NR^{7l}R^{15l}$ where
$r^l$ and $s^l$ are independently 0 to 3;
$B^l$ is absent; —O—; —S—; or —NR$^{8l}$—;
where $R^{8l}$ is hydrogen; loweralkyl; alkanoyl; or aroyl; and
$R^{7l}$ is

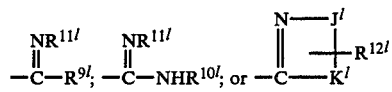

where
$R^{9l}$ is loweralkyl; aralkyl; aryl; heteroaryl; or heteroarloweralkyl and these groups substituted by hydroxy, lower alkoxy or halo; carboxyl; carboxamido; nitromethenyl.
$R^{10l}$ is hydrogen; loweralkyl; aryl; or amidino;
$R^{11l}$ is hydrogen; loweralkyl cyano; amidino; aryl; aroyl; loweralkanoyl;

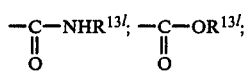

—NO$_2$; —SO$_2$NH$_2$;
or SO$_2$R$^{13l}$;
$R^{12l}$ is hydrogen; loweralkyl; halo; aralkyl; amino; cyano; mono- or diloweralkylamino; or $OR^{4l}$;
$R^{13l}$ is hydrogen; loweralkyl; or aryl;
$R^{15l}$ is hydrogen; lower alkyl; aralkyl; or aryl;

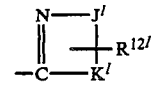

constitute a basic heterocycle of 5 or 6 atoms or benzofused analogs thereof and optionally containing 1–3 N atoms, an oxygen, a sulfur, an S=O, or an SO$_2$ group and optionally substituted by amino, lower alkyl amino, diloweralkyl amino, lower alkoxy, or aralkyl groups;
$R^{3l}$ is C$_{3-8}$ cycloalkyl and benzofused C$_{3-8}$ cycloalkyl; perhydrobenzofused C$_{3-8}$ cycloalkyl; aryl; substituted aryl; heteroaryl; substituted heteroaryl;
$R^{14l}$ is hydrogen or loweralkyl; and, a pharmaceutically acceptable salt thereof.

U.S. Pat. No. 4,256,761 to Suh et al discloses amides which are angiotensin converting enzyme inhibitors and have the general formula

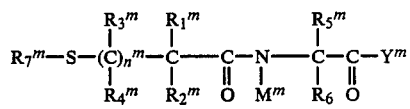

wherein
$R_1^m$, $R_2^m$, $R_3^m$, $R_4^m$, $R_5^m$ and $R_6^m$ are hydrogen, alkyl, alkenyl, alkynyl, phenyl-alkyl, and cycloalkyl, and may be the same or different,
$n^m$ is an integer from 0 to 4 inclusive,
$M^m$ is alkenyl, alkynyl, cycloalkyl, cycloalkylalkyl, polycycloalkyl, polycycloalkyl-alkyl, aryl, aralkyl, heteroaryl, heteroaryl-alkyl, hetero-cycloalkyl, heterocycloalkyl-alkyl, fused aryl-cycloalkyl, fused aryl-cycloalkyl-alkyl, fused heteroaryl-cycloalkyl, fused heteroaryl-cycloalkyl-alkyl, alkoxyalkyl, alkylthioalkyl, alkylamino-alkyl, or dialkylaminoalkyl,
$Y^m$ is hydroxy, alkoxy, amino, or substituted amino, aminoalkanoyl, aryloxy, aminoalkoxy, or hydroxyalkoxy, and
$R_7^m$ is hydrogen, alkanoyl, carboxyalkanoyl, hydroxyalkanoyl, aminoalkanoyl, cyano, amidino, carbalkoxy, $Z^mS$ or

wherein $Z^m$ is hydrogen, alkyl, hydroxyalkyl, or the radical

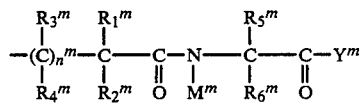

wherein $R_1^m$, $R_2^m$, $R_3^m$, $R_4^m$, $R_5^m$, $R_6^m$, $n^m$, $M^m$ and $Y^m$ are as described above; and where Y is hydroxy, their non-toxic, pharmaceutically acceptable alkali metal, alkaline earth metal, and amine salts.

U.S. Pat. No. 4,344,949 to Hoefle et al discloses acyl derivatives of 1,2,3,4-tetrahydroisoquinoline-3-carboxylic acid compounds which are angiotensin converting enzyme inhibitors and have the formula

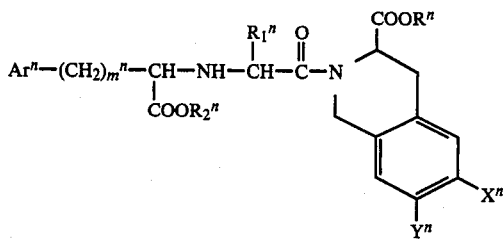

wherein $R^n$ is hydrogen, lower alkyl or aralkyl; $R_1^n$ is hydrogen, lower alkyl, or benzyl; $R_2^n$ is hydrogen or lower alkyl, and $Ar^n$ is phenyl or phenyl substituted with 1 or 2 substituents selected from the group consisting of fluorine, chlorine bromine, lower alkyl, lower alkoxy, hydroxy or amino; $X^n$ and $Y^n$ are independently hydrogen, lower alkyl, lower alkoxy, lower alkylthio, lower alkylsulfinyl, lower alkylsulfonyl, hydroxy, or $X^n$ and $Y^n$ together are methylenedioxy; $m^n$ is 0 to 3; and the pharmaceutically acceptable acid salts thereof.

European Pat. No. 79022 published May 18, 1983 discloses N-amino acyl-azabicyclooctane carboxylic acid derivatives which have the formula

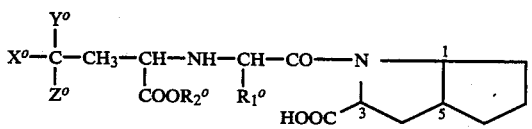

hydrogen atoms at ring positions 1 and 5 are cis to each other and the 3-carboxy group has the endo orientation;

$R_1^o$ is H, allyl, vinyl or the side chain of an optionally protected naturally occurring a-amino acid;

$R_2^o$ is H, 1-6C alkyl, 2-6C alkenyl or aryl(1-4C alkyl);

$Y^o$ is H or OH and $Z^o$ is H, or $Y^o$ and $Z^o$ together are oxygen;

$X^o$ is 1-6C alkyl, 2-6C alkenyl, 5-9C cycloalkyl, 6-12C aryl (optionally substituted by one to three 1-4C alkyl or alkoxy, OH, halo, nitro, amino (optionally substituted by one or two 1-4C alkyl), or methylenedioxy) or indol-3-yl.

European Pat. No. 46953 published March 10, 1982 discloses N-amino acyl-indoline and tetrahydro isoquinoline carboxylic acids which are angiotensin coverting enzyme inhibitors and have the formula

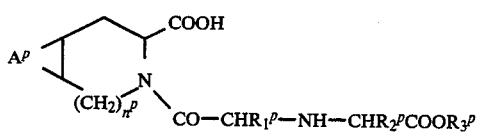

$n^p$ is 0 or 1;

is a benzene or cyclohexane ring:

$R_1^p$ and $R_2^p$ are each 1-6C alkyl, 2-6C alkenyl, 5-7C cycloalkyl, 5-7C cycloalkenyl, 7-12C cycloalkylalkyl, optionally partially hydrogenated 6-10C aryl, 7-14C aralkyl or 5-7 membered monocyclic or 8-10 membered bicyclic heterocyclyl containing 1 or 2 S or 0 and/or 1-4N atoms; all $R_1^p$ and $R_2^p$ groups are optionally substituted. $R_3^p$ is H, 1-6C alkyl, 2-6C alkenyl or 7-14C aralkyl.

Preferred $R_1^p$ is Me and $R_2^p$ is phenethyl optionally substituted by halogen, Me or OMe.

U.S. Pat. No. 4,508,729 to Vincent et al. discloses substituted imino-acids which are angiotensin converting enzyme inhibitors and have the formula

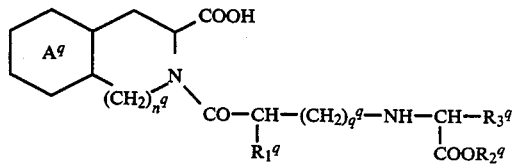

wherein:

the ring $A^q$ is saturated and $n^q=0$ or 1, or the ring $A^q$ is a benzene ring and $n^q=1$, $R_1^q$ represents a lower alkyl group having from 1 to 4 carbon atoms which can carry an amino group, $R_2^q$ represents a hydrogen atom or a alkyl group having from 1 to 4 carbon atoms, $R_3^q$ represents a straight or branched alkyl group, a mono- or dicycloalkylalkyl or phenylalkyl group having no more than a total of 9 carbon atoms, or a substituted alkyl group of the formula:

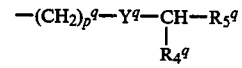

with $R_4^q=H$, a lower alkyl ($C_1$ to $C_4$) or a cycloalkyl ($C_3$ to $C_6$ group, $R_5^q=H$, a lower alkyl ($C_1$ to $C_4$) a cycloalkyl ($C_3$ to $C_6$) or an alkoxycarbonyl group, $Y^q=S$ or $>N-Q^q$ where $Q^q=H$, or an acetyl or benzyloxycarbonyl group, and $p^q=1$ or 2, and $q^q=0$ or 1, and the pharmaceutically acceptable salts thereof.

U.S. Pat. No. 4,512,924 to Attwood et al. discloses bicyclic compounds which are angiotensin converting enzyme inhibitors and have the formula

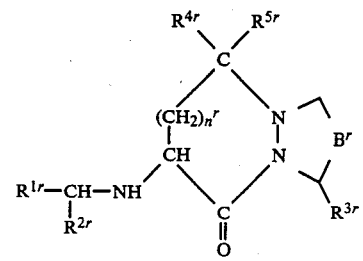

wherein $B^r$ represents a methylene ($-CH_2-$), ethylene ($-CH_2-CH_2-$) or vinylene ($-CH=CH-$) group, $R^{1r}$ represents a hydrogen atom or an alkyl, aralkyl, aminoalkyl, monoalkylamino-alkyl, dialkylamino-alkyl, acylamino-alkyl, phthalimido-alkyl, alkoxycarbonylaminoalkyl, aryloxycarbonyl-aminoalkyl, aralkoxycarbonylamino-alkyl, alkylaminocarbonylamino-alkyl, arylaminocarbonylamino-alkyl, aralkylaminocarbonylaminoalkyl, alkylsulphonylamino-alkyl or arylsulphonylaminoalkyl group, $R^{2r}$ represents a carboxyl, alkoxycarbonyl or aralkoxycarbonyl group or a group of the formula $$-\overset{O}{\underset{OH}{\overset{\|}{P}}}{\overset{OH}{\diagup}} \quad \text{or} \quad -\overset{O}{\overset{\|}{C}}{\diagdown}\underset{\underset{R^{7r}}{|}}{N}-R^{6r}$$

$R^{3r}$ represents a carboxyl, alkoxycarbonyl or aralkoxycarbonyl group, $R^{4r}$ and $R^{5r}$ each represent a hydrogen atom or $R^{4r}$ and $R^{5r}$ together represent an oxo group, $R^{6r}$ and $R^{7r}$ each represent a hydrogen atom or an alkyl or aralkyl group or $R^{6r}$ and $R^{7r}$ together with the nitrogen atom to which they are attached represent a saturated 5 membered or 6-membered heteromonocyclic ring which may contain a further nitrogen atom or an oxygen or sulphur atom, and $n^r$ stands for zero, 1 or 2, and pharmaceutically acceptable salts thereof.

U.S. Pat. No. 4,410,520 to Watthey discloses 3-amino-[1]benzazepin-2-one-1-alkanoic acids which are angiotensin converting enzyme inhibitors and have the formula wherein $R_A{}^s$ and $R_B{}^s$ are radicals of the formula $$-CH{\diagdown}\underset{R_0{}^s}{\overset{R_1{}^s}{\diagup}} \quad \text{and} \quad -CH{\diagdown}\underset{R_0{}^s}{\overset{R_2{}^s}{\diagup}}$$

respectively in which $R_0{}^s$ is carboxy or a functionally modified carboxy;

$R_1{}^s$ is hydrogen, lower alkyl, amino(lower)alkyl, aryl, aryl(lower)alkyl, cycloalkyl or cycloalkyl(lower)alkyl;

$R_2{}^s$ is hydogen or lower alkyl;

$R_3{}^s$ and $R_4{}^s$, each independently, represent hydrogen, lower alkyl, lower alkoxy, lower alkanoyloxy, hydroxy, halogen, trifluoromethyl, or $R_3{}^s$ and $R_4{}^s$ taken together represent lower alkylenedioxy;

$R_5{}^s$ is hydrogen or lower alkyl, and $X^s$ represents oxo, two hydrogens, or one hydroxy together with one hydrogen; and wherein the carbocyclic ring may also be hexahydro or 6, 7, 8, 9-tetrahydro, and salts and complexes thereof.

U.S. Pat. No. 4,374,847 to Gruenfeld discloses 1-carboxy-(alkanoyl or aralkanoyl)-indolene-2-carboxylic acids which are angiotensin converting enzyme inhibitors and have the formula $$Ph^t-\overset{R_3{}^t}{\underset{\underset{CO-C_nH_{2n^t-1}-R_0{}^t}{|}}{\overset{|}{C}-R_2{}^t}}{\diagdown}\underset{COOH}{\overset{COOH}{\diagup}}$$

wherein $Ph^t$ is unsubstituted 1,2-phenylene, or 1,2-phenylene substituted by one to three identical or different members selected from lowr alkyl, lower alkoxy, lower alkylenedioxy, hydroxy, halogeno and trifluoromethyl; $R_0{}^t$ is hydrogen or $HPh^t$; each of $R_1{}^t$, $R_2{}^t$ and $R_3{}^t$ is hydrogen or lower alkyl; and $n^t$ is an integer from 1 to 10; the amides, mono- or di-lower alkylamides, lower alkyl esters, (amino, mono- or di-lower alkylamino, carboxy or lower carbalkoxy)-lower alkyl esters, or pharmaceutically acceptable salts thereof.

As indicated by Needleman et al., a number of atrial peptides have been isolated so far, all having the same core sequence of 17 amino acids within a cysteine disulfide bridge, but having different N-termini lengths. These peptides represent N-terminal truncated fragments (21–48 amino acids) of a common preprohormone (151 and 152 amino acids for man and rats, respectively). Human, porcine and bovine carboxy-terminal 28-amino acid peptides are identical and differ from similar peptides in rats and mice in that the former contain a methionine group at position 12 while the latter contain isoleucine. Various synthetic analogs of naturally occurring atrial peptides also have been found to have comparable biological activity. Examples of atrial peptides contemplated for use in this invention are α human AP 21 (atriopeptin I), α human AP 28, α human AP 23 (atriopeptin II or APII), α human AP 24, α human AP 25, α human AP 26, α human AP 33, and the corresponding rat sequence at each of the above wherein met 12 is ile. See Table 1 for a comparison of the peptides.

TABLE 1

| Human Peptide | AP 33 | AP 28 | AP 26 | AP 25 | AP 24 | AP 23 | AP 21 |
|---|---|---|---|---|---|---|---|
| Leu | | | | | | | |
| Ala | | | | | | | |
| Gly | | | | | | | |
| Pro | | | | | | | |
| Arg | | | | | | | |
| Ser | | Ser | | | | | |
| Leu | | | | | | | |
| Arg | | | Arg | | | | |
| Arg | | | | Arg | | | |
| Ser | | | | | Ser | Ser | Ser |
| Ser | | | | | | | |
| Cys—S | | | | | | | |
| Phe | | | | | | | |
| Gly | | | | | | | |
| Gly | | | | | | | |
| Arg | | | | | | | |
| Met* | | | | | | | |
| Asp | | | | | | | |
| Arg | | | | | | | |

TABLE 1-continued

| Human Peptide | | | | | |
|---|---|---|---|---|---|
| Ile Gly Ala Gln | | | | | |
| Ser Gly Leu Gly ⎣Cys—S | | | | | |
| Asn Ser Phe Arg Tyr | Tyr | Tyr | Tyr | Tyr | Ser Arg |

*Ile in the rat peptide

The antihypertensive effect of NMEP inhibitors, alone and in combination with ACE inhibitors was determined according to the following procedure:

Male Sprague Dawley rats weighing 100-150 g were anesthetized with ether and the right kidney was removed. Three pellets containing Doc acetate (desoxycorticosterone acetate, DOCA, 25 mg/pellet) were implanted subcutaneously. Animals recovered from surgery, were maintained on normal rat chow and were allowed free access to a fluid of 1% NaCl and 0.2% KCl instead of tap water for a period of 25-30 days. This procedure results in a sustained elevation in blood pressure and is a slight modification of published procedures (e.g. Brock et al., 1982) that have been used to produce DOCA salt hypertension in the rat.

On the day of study, animals were again anesthetized with ether and the caudal artery was cannulated for blood pressure measurement. Patency of the caudal artery cannula was maintained with a continuous infusion of dextrose in water at a rate of 0.2 ml/hr. Animals were placed into restraining cages where they recovered consciousness. Blood pressure was measured from caudal artery catheter using a Statham pressure transducer attached to a Beckman oscillographic recorder. In addition, a cardiovascular monitoring device (Buxco Electronics, Inc.) and a digital computer were used to calculate average blood pressures.

After an equilibration period of at least 1.5 hr., animals were dosed subcutaneously (1 ml/kg) with vehicle (methylcellulose, hereinafter MC), NMEP inhibitor, ACE inhibitor, or the combination of NMEP inhibitor and ACE inhibitor and blood pressure was monitored for the next 4 hours. The doses of NMEP inhibitor and ACE inhibitor are chosen based on amounts previously determined to be effective for inhibition of enkephalinase A and ACE, respectively.

The antihypertensive effect of NMEP inhibitors in combination with atrial peptides was determined according to the following procedures:

Male spontaneously hypertensive rats (SHR), 16-18 weeks old, 270-350 g, were anesthetized with ether and the abdominal aorta was cannulated through the tail artery. The animals were then placed into restrainers to recover from anesthesia (in less than 10 min.) and remained inside throughout the experiments. Through a pressure transducer (Gould P23 series) analog blood pressure signals were registered on a Backman 612 recorder. A Buxco digital computer was used to obtain mean arterial pressures. Patency of the arterial cannula was maintained with a continuous infusion of 5% dextrose at 0.2 ml/hr. Animals were allowed a 90-min equilibration period. The animals first underwent a challenge with an atrial peptide such as atriopeptin II (AP II) or AP28 30 μg/kg iv and at the end of 60 min. were treated with MC vehicle or various enzyme inhibitors subcutaneously. A second atrial peptide challenge was administered 15 min. later and blood pressure was monitored for the next 90 min.

The antihypertensive effect in SHR of NMEP inhibitors and ACE inhibitors, alone and in combination, was determined as follows:

Animals were prepared for blood pressure measurement as described above. After stabilization, animals were dosed subcutaneously with test drugs or placebo and blood pressure was monitored for the next 4 hr.

The compositions of this invention comprise an NMEP inhibitor, an NMEP inhibitor and an ACE inhibitor, or an NMEP inhibitor and an atrial peptide in combination with a pharmaceutically acceptable carrier for administration to mammals. A variety of pharmaceutical forms is suitable, preferably for oral or parenteral administration, although mechanical delivery systems such as transdermal dosage forms are also contemplated.

The daily antihypertensive dose of the compound or combinations of this invention is as follows: for NMEP inhibitor alone the typical dosage is 1 to 100 mg/kg of mammalian weight per day administered in single or divided dosages; for the combination of NMEP inhibitors and ACE inhibitors, the typical dosage is 1 to 100 mg of NMEP inhibitor/kg of mammalian weight per day, in single or divided dosages, plus 0.1 to 30 mg ACE inhibitor/kg of mammalian weight per day in single or divided dosages; for the combination of NMEP inhibitor and atrial peptide, the typical dosage is 1 to 100 mg of NEMP inhibitor/kg mammalian weight per day in single or divided dosages plus 0.001 to 0.1 mg atrial peptide/kg of mammalian weight per day, in single or divided doses. The exact dose of any component or combination to be administered is determined by the attending clinician and is dependent on the potency of the compound administered, the age, weight, condition and response of the patient.

Generally, in treating humans having hypertension, the compounds or combinations of this invention may be administered to patients in a dosage range as follows: for treatment with NMEP inhibitors alone, about 10 to about 500 mg per dose given 1 to 4 times a day, giving a total daily dose of about 10 to 2000 mg per day; for the combination of NMEP inhibitor and ACE inhibitor, about 10 to about 500 mg NMEP inhibitor per dose given 1 to 4 times a day and about 5 to about 50 mg ACE inhibitor given 1 to 3 times a day (total daily dosage range of 10 to 2000 mg/day and 5 to 150 mg per day, respectively); for the combination of NMEP inhibitor and atrial peptide, about 10 to about 500 mg NMEP inhibitor per dose given 1 to 4 times a day and about 0.001 to about 1 mg atrial peptide given 1 to 6 times a day (total daily dosage range of·10 to 2000 mg day and 0.001 to 6 mg/day, respectively). Where the components of a combination are administered separately, the number of doses of each component given per day may not necessarily be the same, e.g. where one component may have a greater duration of activity, and will therefore need to be administered less frequently.

Typical oral formulations include tablets, capsules, syrups, elixirs and suspensions. Typical injectable formulations include solutions and suspensions.

The typical acceptable pharmaceutical carriers for use in the formulations described above are exemplified by: sugars such as lactose, sucrose, mannitol and sorbitol, starches such as cornstarch, tapioca starch and potato starch; ceullulose and derivatives such as sodium carboxymethyl cellulose, ethyl cellulose and methyl cellulose; calcium phosphates such as dicalcium phosphate and tricalcium phosphate; sodium sulfate; calcium sufate; polyvinylpyrrolidone, polyvinyl alcohol; stearic acid; alkaline earth metal stearates such as magnesium stearate and calcium stearate, stearic acid, vegetable oils such as peanut oil, cottonseed oil, sesame oil, olive oil and corn oil; non-ionic, cationic and anionic surfactants; ethylene glycol polymers; betacyclodextrin; fatty alcohols and hydrolyzed cereal solids; as well as other nontoxic compatible fillers, binders, disintegrants, buffers, preservatives, antioxidants, lubricants, flavoring agents, and the like commonly used in pharmaceutical formulations.

Since the present invention relates to treatment of hypertension with combinations of active ingredients wherein said active ingredients may be administered separately, the invention also relates to combining separate pharmaceutical compositions in kit form. That is, two kits are contemplated, each combining two separate units: an NMEP inhibitor pharmaceutical composition and an ACE inhibitor pharmaceutical composition in one kit, and an NMEP inhibitor pharmaceutical composition and an atrial peptide pharmaceutical composition in a second kit. The kit form is particularly advantageous when the separate components must be administered in different dosage forms (e.g. oral and parenteral) or are administered at different dosage intervals.

The above descriptions on pages 4–47 inclusive, of suitable classes of NMEP inhibitors and ACE inhibitors for use in the present invention were taken from the noted patents and publications or abstracts thereof. Reference should be made to such patents and publications themselves for their full disclosures of such classes and specific compounds within such classes, such patents and publications being incorporated herein by reference for such purposes, and as to any typographical errors or the like which may have occurred in transcription. Also, in describing such suitable NMEP inhibitors and ACE inhibitors the superscript letters a-v were included to distinguish among the various classes of compounds and the variable substituent groups thereof.

We claim:

1. A method for treating hypertension in mammals comprising administering to a mammal in need of such treatment an antihypertensive effective amount of a neutral metalloendopeptidase inhibitor in a pharmaceutically acceptable carrier.

2. A method of claim 1 wherein the neutral metalloendopeptidase inhibitor is chosen from:
N-[N-[L-1-(2,2-dimethyl-1-oxopropoxy)methoxy]-carbonyl]-2-phenylethyl]-L-phenylalanyl]-β-alanine (2,2-dimethyl-1-oxopropoxy)methyl ester;
N-[N-[(L-1-carboxy-2-phenylethyl)]-L-phenylalanyl]-β alanine;
N-[1-oxo-3-phenyl-2-(phosphonomethyl)propyl]-β-alanine; and
N-[1-oxo-3-phenyl-2-(phosphonomethyl)propyl]-β-alanine ethyl ester.

3. A method of claim 1 wherein the antihypertensive effective amount of neutral metalloendopeptidase inhibitor is 1 to 100 mg/kg of mammalian weight per day.

4. A method for treating hypertension in mammals which comprises administering to a mammal in need of such treatment an antihypertensive effective amount of a combination of a neutral metalloendopeptidase inhibitor and an atrial peptide.

5. A method of claim 4 wherein the neutral metalloendopeptidase inhibitor is chosen from:
N-[N-[L-1-(2,2-dimethyl-1-oxopropoxy)methoxy]-carbonyl]-2-phenylethyl]-L-phenylalanyl]-β-alanine (2,2-dimethyl-1-oxopropoxy)methyl ester;
N-[N-[(L-1-carboxy-2-phenylethy)]-L-phenylalanyl]-β alanine;
N-[1-oxo-3-phenyl-2-(phosphonomethy)propyl]-β-alanine; and
N-[1-oxo-3-phenyl-2-(phosphonomethyl)propyl]-β-alanine ethyl ester.

6. A method of claim 4 wherein the atrial peptide is chosen from α human AP 21, α human AP 28, α human AP 23, α human AP 24, α human AP 25, α human AP 26, α human AP 33, and the corresponding atrial peptides wherein the methionine at position 12 is replaced by isoleucine.

7. A method of claim 4 wherein the neutral metalloendopeptidase inhibitor is chosen from:
N-[N-[L-1-(2,2-dimethyl-1-oxopropoxy)methoxy]-carbonyl]-2-phenylethyl]-L-phenylalanyl]-β-alanine (2,2-dimethyl-1-oxopropoxy)methyl ester;
N-[N-[(L-1-carboxy-2-phenylethyl)]-L-phenylalanyl]-β alanine;
N-[1-oxo-3-phenyl-2-(phosphonomethyl)propyl]-β-alanine; and
N-[1-oxo-3-phenyl-2-(phosphonomethyl)propyl]-β-alanine ethyl ester,
and the atrial peptide is chosen from α human AP 21, α human AP 28, α human AP 23, α human AP 24, α human AP 25, α human AP 26, α human AP 33, and the corresponding atrial peptides wherein the methionine at position 12 is replaced by isoleucine.

8. A method of claim 4 wherein the neutral metalloendopeptidase inhibitor is administered at a dosage level of 1 to 100 mg/kg mammalian weight per day and the atrial peptide is administered at a dosage level of 0.001 to 0.1 mg/kg mammalian weight per day.

9. A pharmaceutical composition comprising an antihypertensive effective amount of a combination of a neutral metalloendopeptidase inhibitor and an atrial peptide in a pharmaceutically acceptable carrier.

10. A method for treating hypertension in mammals which comprises administering to a mammal in need of such treatment an antihypertensive effective amount of a combination of a neutral metalloendopeptidase inhibitor and an angiotensin converting enzyme inhibitor.

11. A method of claim 10 wherein the angiotensin converting enzyme inhibitor is selected from: a compound of the formula

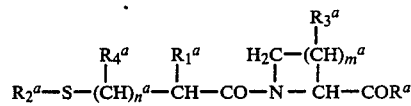

wherein
$R^a$ is hydroxy, $NH_2$ or lower alkoxy;

$R_1{}^a$ and $R_4{}^a$ each is hydrogen, lower alkyl, phenyl or phenyl-lower alkyl;

$R_2{}^a$ is hydrogen, lower alkyl, phenyl, sustituted phenyl wherein the phenyl substituent is halo, lower alkyl or lower alkoxy, phenyl-lower alkyl, diphenyl-lower alkyl, triphenyl-lower alkyl, lower alkylthiomethyl, phenyl-lower alkylthiomethyl, lower alkanoyl-amidomethyl,

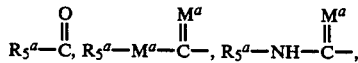

$R_4{}^a$—S—, or $R_f{}^a$ $R_3{}^a$ is hydrogen, hydroxy or lower alkyl;

$R_5{}^a$ is lower alkyl, phenyl or phenyl-lower alkyl;

$R_6{}^a$ is lower alkyl, phenyl, substituted phenyl (wherein the phenyl substituent is halo, lower alkyl or lower alkoxy), hydroxy-lower alkyl or amino(-carboxy)lower alkyl;

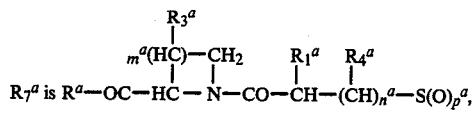

$M^a$ is O or S;

$m^a$ is 1 to 3;

$m^a$ and $p^a$ each is 0 to 2; a compound of the formula

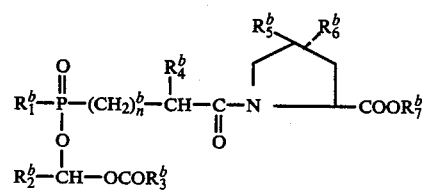

$R_1{}^b$ is alkyl, aryl, aralkyl, cycloalkyl or cycloalkylalkyl;

$R_2{}^b$ is cycloalkyl, 3-cyclohexenyl or 2-alkyl-3-cyclohexenyl;

$R_3{}^b$ is alkyl, cycloalkyl or phenyl;

$R_4{}^b$ is H or alkyl; One of $R_5{}^b$ and $R_6{}^b$ is H and the other is alkyl—$X^b$—, phenyl—$X^b$—alkoxy, phenoxy, phenyl, cycloalkyl, alkyl or phenylalkyl; or $R_5{}^b$ and $R_6{}^b$ together form —$X^b CH_2CH_2X^b$—, $X^b$ is S, SO or $SO_2$;

$R_7{}^b$ is H or $CH(R_2{}^b)OCOR_3{}^b$;

$n^b$ is 0 or 1;

'aryl' is phenyl opt. substituted by halo, alkyl, alkoxy, alkylthio, OH, alkanoyl, $NO_2$, amino, dialkylamino and/or $CF_3$;

alkyl has 1–10C, cycloalkyl 3–7C, alkoxy 1–8C and alkanoyl 2–9C;

a compound of the formula

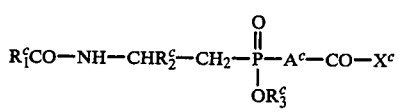

$R_1{}^c$ and $R_2{}^c$ are H, 1–7C alkyl, 1–7C haloalkyl, $(CH_2)_m{}^c$—$D^c$, 1–7C aminoalkyl or a group of formula:

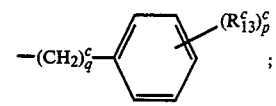

$D^c$ is cycloalkyl, furyl, thienyl or pyridinyl;

$A^c$ is $(CH_2)_N$—$CHR_{21}{}^c$, $NR_{22}{}^c$—$CHR_{23}{}^c$ or O—$CHR_{23}{}^c$;

$n^c$ is 0 or 1;

$q^c$ is 0–7;

$R_{21}{}^c$ is H, 1–7C alkyl, 1–7C haloalkyl, benzyl or phenethyl;

$R_{22}{}^c$ is H or 1–7C alkyl;

$R_{23}{}^c$ is H, 1–7C alkyl, 1–7C haloalkyl or $(CH_2)_r{}^c D_1{}^c$;

$D_1{}^c$ is phenyl, 4-hydroxyphenyl, 3,4-dihydroxyphenyl, 3-indolyl, 4-imidazolyl, $NH_2$, SH, 1–7C alkylthio, guanidino or $CONH_2$;

$X^c$ is a group of formula $(II)^c$–$(V)^c$, or $NR_4{}^c$—$CHR_5{}^c$—$COOR_6{}^c$;

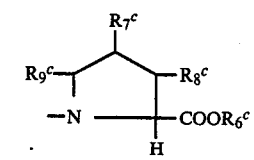

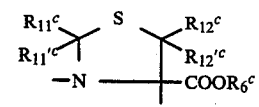

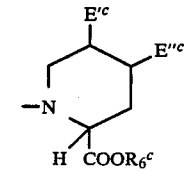

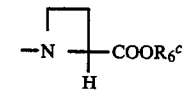

where $R_9{}^c$ and $R_8{}^c$ are H and $R_7{}^c$ is as defined below;

$R_9{}^c$ and $R_7{}^c$ are H and $R_8{}^c$ is as defined below;

$R_7{}^c$ and $R_8{}^c$ are H and $R_9{}^c$ is as defined below;

$R_9{}^c$ and $R_8{}^c$ are H and —$CHR_7{}^c$— is replaced by —$CR_{10}{}^c R_{10}{}^c$;

$R_9{}^c$ is H and $R_7{}^c + R_8{}^c$ form a double bond;

$R_9{}^c$ is H and $R_7{}^c + R_8{}^c$ complete a fused benzene ring; or $R_8{}^c$ is H and $R_9{}^c + R_7{}^c$ complete a fused benzene ring;

$E'^c$ and $E''^c$ are H or $E'^c + E''^c$ complete a fused benzene ring;

$R_7{}^c$ is H, 1–7C alkyl, halogen, keto, OH, 2–8C alkanoyl-amino, $N_3$, $NH_2$, $NR_{19}{}^c R_{20}{}^c$, $(CH_2)_m{}^c$-$D^c$, O—$CONR_{15}{}^c R_{15}{}^c$, 1–7C alkoxy, 1–7C alkylthio, or a group of formula $(VI)^c$, $(VII)^c$ or $(VIII)^c$:

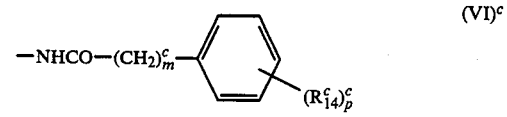

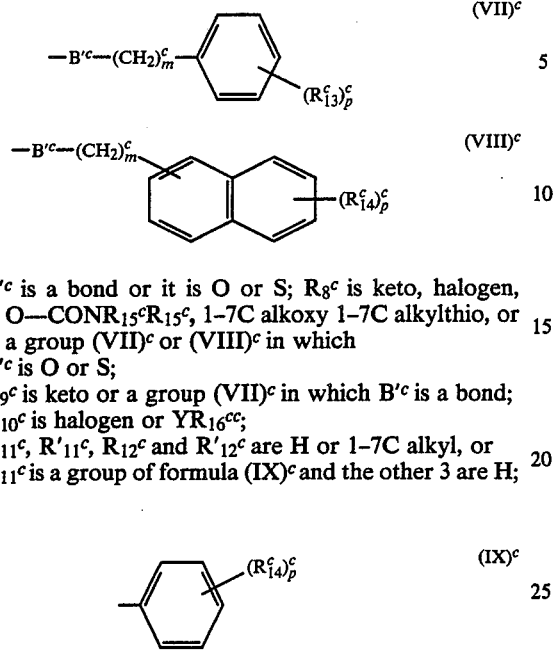

$B'^c$ is a bond or it is O or S; $R_8^c$ is keto, halogen, O—$CONR_{15}^c R_{15}^c$, 1-7C alkoxy 1-7C alkylthio, or a group $(VII)^c$ or $(VIII)^c$ in which
$B'^c$ is O or S;
$R_9^c$ is keto or a group $(VII)^c$ in which $B'^c$ is a bond;
$R_{10}^c$ is halogen or $YR_{16}^{cc}$;
$R_{11}^c$, $R'_{11}^c$, $R_{12}^c$ and $R'_{12}^c$ are H or 1-7C alkyl, or $R_{11}^c$ is a group of formula $(IX)^c$ and the other 3 are H;

$R_{13}^c$ is H, 1-4C alkyl, 1-4C alkoxy, 1-4C alkylthio, Cl, Br, F, $CF_3$, OH, Ph, PhO, PhS or $PhCH_2$;
$R_{14}^c$ is H, 1-4C alkyl, 1-4C alkoxy, 1-4C alkylthio, Cl, Br, F, $CF_3$ or OH;
$m^c$ is 0-3;
$p^c$ is 1-3 but it is 2 or 3 only when $R_{13}^c$ or $R_{14}^c$ is H, Me, MeO, Cl or F;
$R_{15}^c$ is H or 1-4C alkyl;
$Y^c$ is O or S;
$R_{16}^c$ is 1-4C alkyl or group $(VII)^c$ in which $B'^c$ is a bond; or the two $R_{16}^c$ groups complete a 5- or 6-membered ring in which the C atoms may each bear 1 or 2 alkyls having 1-4C;
$R_4^c$ is H, 1-7C alkyl, cycloalkyl or $(CH_2)^c$—Ph;
$R_5^c$ is H, 1-7C alkyl or $(CH_2)_{r^c}$-$D_1^c$; $r^c$ is 1-4;
$R_3^c$ and $R_6^c$ are H, 1-7C alkyl, $PhCH_2$, PhCH or $CHR_{17}^c$—O—$COR_{18}^c$;
$R_{17}^c$ is H, 1-7C alkyl or Ph;
$R_{18}^c$ is H, 1-7C alkyl, 1-7C alkoxy or Ph; or
$R_{17}^c + R_{18}^c$ form $(CH_2)_2$, $(CH_2)_3$, —CH=CH or o-phenylene;
$R_{19}^c$ is 1-7C alkyl, benzyl or phenethyl; and
$R_{20}^c$ is H or chosen as for $R_{19}^c$;
a compound of the formula

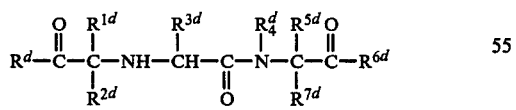

wherein
$R^d$ and $R^{6d}$ are the same or different and are hydroxy, lower alkoxy, lower alkenoxy, dilower alkylamino lower alkoxy (dimethylaminoethoxy), acylamino lower alkoxy (acetylaminoethoxy), acyloxy lower alkoxy (pivaloyloxymethoxy), aryloxy, such as phenoxy, arloweralkoxy, such as benzyloxy, substituted aryloxy or substituted arloweralkoxy wherein the substituent is methyl, halo or methoxy, amino, loweralkylamino, diloweralkylamino, hydroxyamino, arloweralkylamino such as benzylamino;
$R^{1d}$ is hydrogen, alkyl of from 1 to 20 carbon atoms which include branched and cyclic and unsaturated (such as allyl) alkyl groups, substituted loweralkyl wherein the substituent can be halo, hydroxy, lower alkoxy, aryloxy such as phenoxy, amino, diloweralkylamino, acylamino, such as acetamido and benzamido, arylamino, guanidino, imidazolyl, indolyl, mercapto, loweralkylthio, arylthio such as phenylthio, carboxy or carboxamido, carboloweralkoxy, aryl such as phenyl or naphthyl, substituted aryl such as phenyl wherein the substituent is lower alkyl, lower alkoxy or halo, arloweralkyl, arloweralkenyl, heteroarlower alkyl or heteroarlower alkenyl such as benzyl, styryl or indolyl ethyl, substituted arloweralkyl, substituted arloweralkenyl, substituted heteroarlower alkyl, or substituted heteroarlower alkenyl, wherein the substituent(s) is halo, dihalo, lower alkyl, hydroxy, lower alkoxy, amino, aminomethyl, acylamino (acetylamino or benzoylamino) diloweralkylamino, loweralkylamino, carboxyl, haloloweralkyl, cyano or sulfonamido; arloweralkyl or heteroarloweralkyl substituted on the alkyl portion by amino or acylamino (acetylamino or benzoylamino);
$R^{2d}$ and $R^{7d}$ are the same or different and are hydrogen or lower alkyl;
$R^{3d}$ is hydrogen, lower alkyl, phenyl lower alkyl, aminomethyl phenyl lower alkyl, hydroxy phenyl lower alkyl, hydroxy lower alkyl, acylamino lower alkyl (such as benzoylamino lower alkyl, acylamino lower alkyl), amino lower alkyl, dimethylamino lower alkyl, halo lower alkyl, guanidino lower alkyl, imidazolyl lower alkyl, indolyl lower alkyl, mercapto lower alkyl, lower alkyl thio lower alkyl;
$R^{4d}$ is hydrogen or lower alkyl;
$R^{5d}$ is hydrogen, lower alkyl, phenyl, phenyl lower alkyl, hydroxy phenyl lower alkyl, hydroxy lower alkyl, amino lower alkyl, guanidino lower alkyl, imidazolyl lower alkyl, indolyl lower alkyl, mercapto lower alkyl or lower alkylthio lower alkyl;
$R^{4d}$ and $R^{5d}$ may be connected together to form an alkylene bridge of from 2 to 4 carbon atoms, an alkylene bridge of from 2 to 3 carbon atoms and one sulfur atom, an alkylene bridge of from 3 to 4 carbon atoms containing a double bond or an alkylene bridge as above substituted with hydroxy, loweralkoxy, lower alkyl or dilower alkyl;
and the pharmaceutically acceptable salts thereof;
a compound of the formula

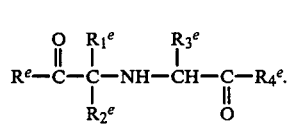

$R_4^e$ is a substituted proline of the formula

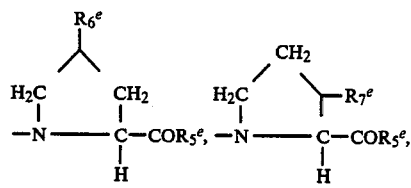
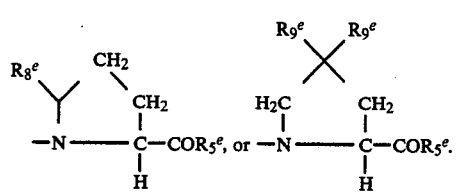
$R_6^e$ is halogen, keto, azido,
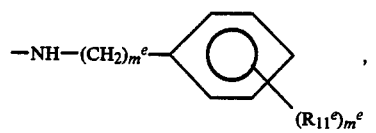
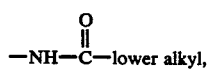
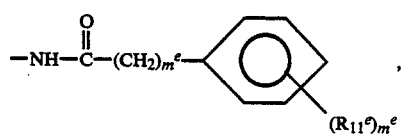
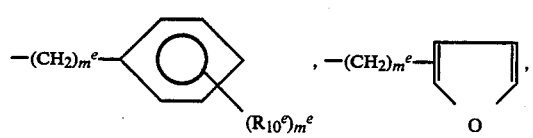
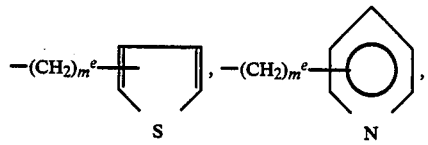
a 1- or 2-naphthyl of the formula
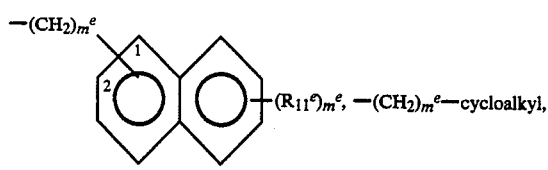
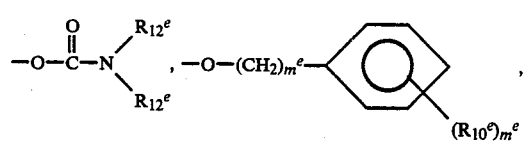
a 1- or 2-naphthyloxy of the formula
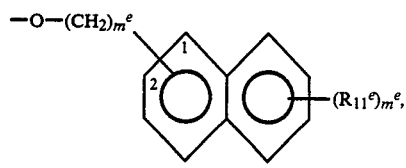
—S—lower alkyl,
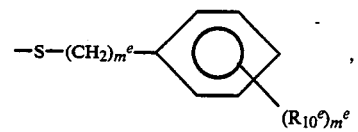
or a 1- or 2-naphthylthio of the formula
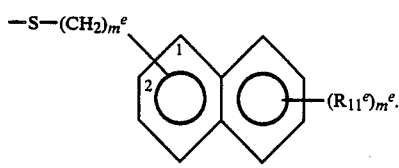
$R_7^e$ is keto, halogen,
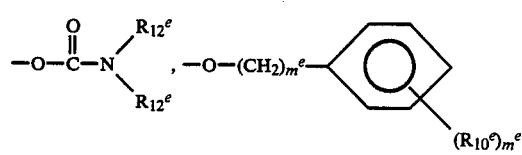
a 1- or 2-naphthloxy of the formula
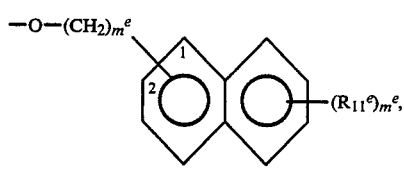
—S—lower alkyl,
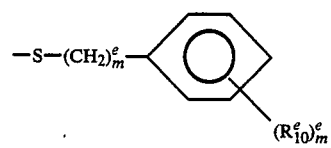
or a 1- or 2-naphthylthio of the formula
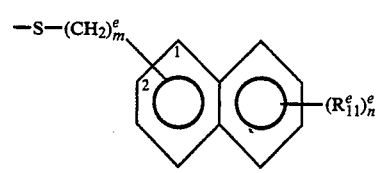
$R_8^e$ is keto or

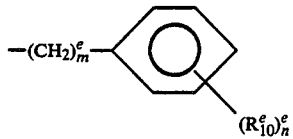

$R_9^e$ is halogen or —$Y^e$—$R_{13}^e$, $m^e$ is zero, one, two, or three, $R_{10}^e$ is hydrogen, lower alkyl of 1 to 4 carbons, lower alkoxy of 1 to 4 carbons, lower alkylthio of 1 to 4 carbons, chloro, bromo, fluor, trifluoromethyl, hydroxy, phenyl, phenoxy, phenylthio, or phenylmethyl, $R_{11}^e$ is hydrogen, lower alkyl of 1 to 4 carbons, lower alkoxy of 1 to 4 carbons, lower alkylthio of 1 to 4 carbons, bromo, fluoro, trifluoromethyl, or hydroxy, $n^e$ is one, two or three provided that $n^e$ is more than one only if $R_{10}^e$ or $R_{11}^e$ is hydrogen, methyl, methoxy, chloro, or fluoro, $R_{12}^e$ is hydrogen or lower alkyl of 1 to 4 carbons, $Y^e$ is oxygen or sulfur, $R_{13}^e$ is lower alkyl of 1 to 4 carbons,

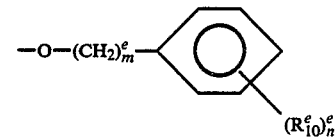

or the $R_{13}^e$ group join to complete an unsubstituted 5- or 6-membered ring or said ring in which one or more of the carbons has a lower alkyl of 1 to 4 carbons, or a di(lower alkyl of 1 to 4 carbons) substituent, $R^e$ and $R_3^e$ are independently selected from hydroxy, lower alkoxy, di(lower alkyl)-amino-lower alkoxy, such as dimethylaminoethoxy, lower alkyl-carbonyl-aminolower alkoxy, such as acetylaminoethoxy, lower alkylcarbonyloxy-lower alkoxy, such as pivaloyloxymethoxy,

wherein $m^e$, $n^e$ and $R_{10}^e$ are as defined above, amino, lower alkyl-amino, di(lower alkyl)-amino, hydroxyamino, benzylamino, or phenethylamino, $R_1^e$ is hydrogen, lower alkyl,

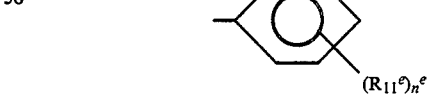

halo substituted lower alkyl, hydroxy substituted lower alky, —(CH$_2$)$_8^e$—cycloalkyl, —(CH$_2$)$_9^e$—carboxy, —(CH$_2$)$_9^e$—S—lower alkyl,

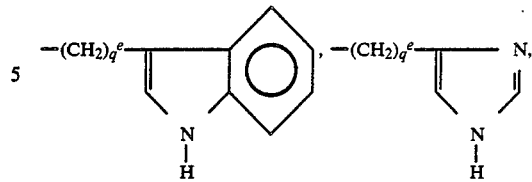

—(CH$_2$)$_q^e$—guanidinyl, —(CH$_2$)$_q^e$—NH$_2$,

—(CH$_2$)$_q^e$—N(lower alkyl)$_2$,

—(CH$_2$)$_q^e$—NH—$\overset{\overset{O}{\|}}{C}$—lower alkyl,

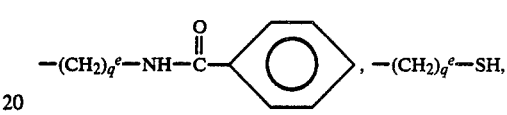

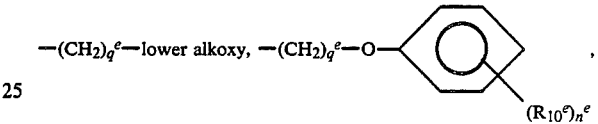

—(CH$_2$)$_q^e$—$\overset{\overset{O}{\|}}{C}$—lower alkoxy, or

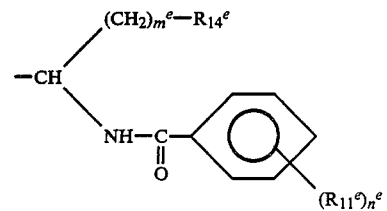

wherein $m^e$, $n^e$, $R_{10}^e$ and $R_{11}^e$ are as defined above, $R_{14}^e$ is lower alkyl, cycloalkyl, or and $q^e$ is an integer from 1 to 4, $R_2^e$ is hydrogen or lower alkyl, $R_3^e$ is hydrogen, lower alkyl, halo substituted lower alkyl, hydroxy substituted lower alkyl, —(CH$_2$)$_9^e$—NH$_2$, —(CH$_2$)$_9^e$13 N-(lower alkyl)$_2$, —(CH$_2$)$_9^e$guanidinyl, —(CH$_2$)$_9^e$—SH, —(CH$_2$)$_9^e$—S—lower alkyl,

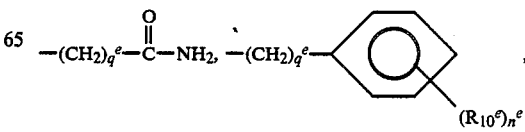

-continued

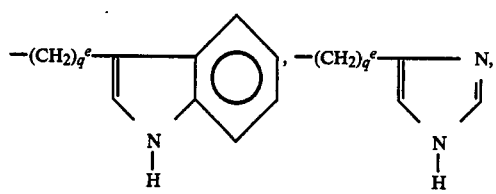

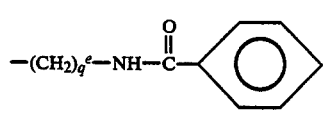

wherein $R_{10}^e$ $n^e$ and $q^e$ are as defined above;
a compound of the formula

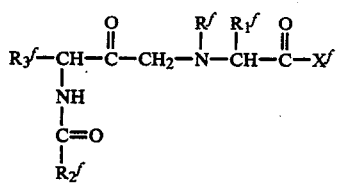

$X^f$ is an amino or imino acid of the formula

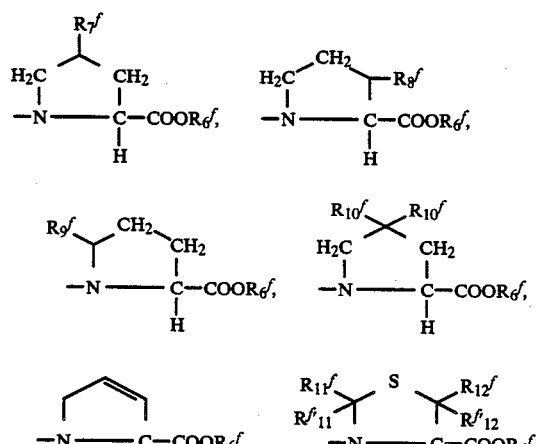

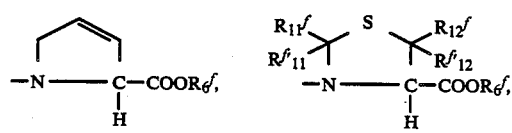

-continued

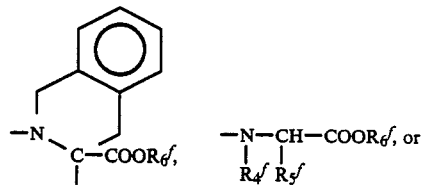

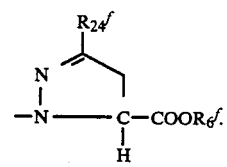

$R^f$ is hydrogen, lower alkyl, cycloalkyl,

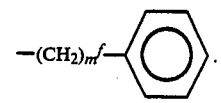

—(CH$_2$)$_2$—NH$_2$, —(CH$_2$)$_3$—NH$_2$, —(CH$_2$)$_4$—NH$_2$,
—(CH$_2$)$_2$—OH, —(CH$_2$)$_3$—OH, —(CH$_2$)$_4$—OH,
—(CH$_2$)$_2$—SH, —(CH$_2$)$_3$—SH or —(CH$_2$)$_4$—SH, $R_1^f$ is hydrogen, lower alkyl, halo substituted lower alkyl,

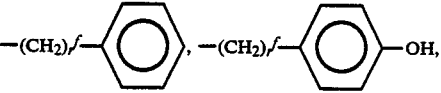

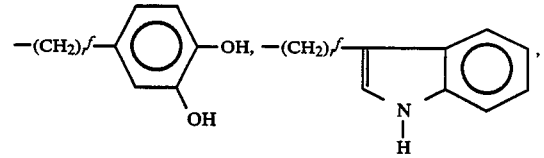

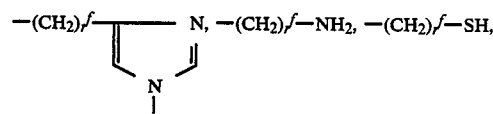

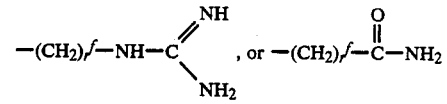

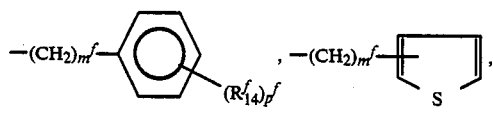

provided that $R_1^f$ is hydrogen only if $R^f$ is other than hydrogen,
$R_2^f$ is

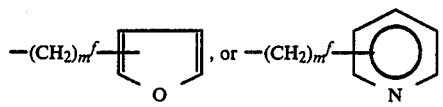
$R_3{}^f$ is hydrogen, lower alkyl,
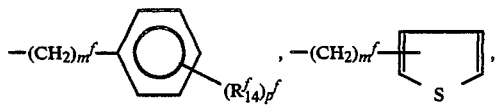
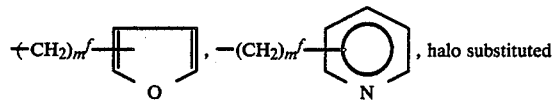, halo substituted
lower alkyl, $-(CH_2)_m{}^f-$cycloalkyl, 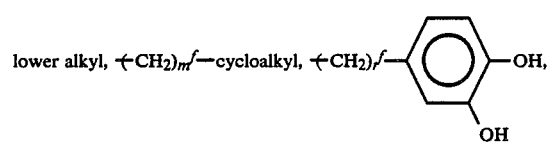
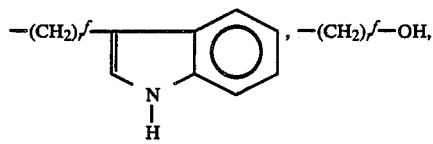, $-(CH_2)_r{}^f-$OH,
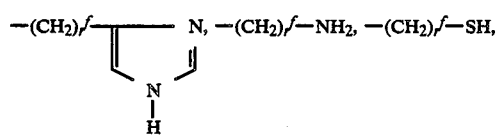
$-(CH_2)_r{}^f-$S—lower alkyl, 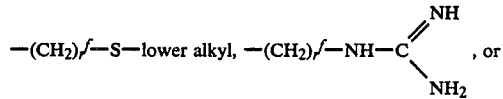, or
$R_4{}^f$ is hydrogen, lower alkyl,
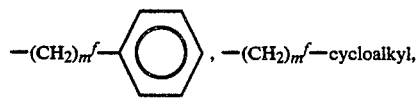, $-(CH_2)_m{}^f-$cycloalkyl,
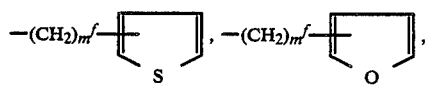,
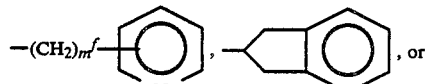, or
$R_5{}^f$ is hydrogen, lower alkyl,
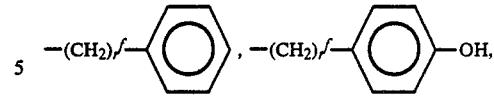
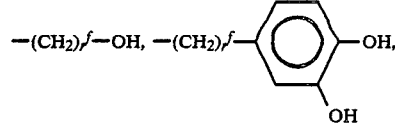
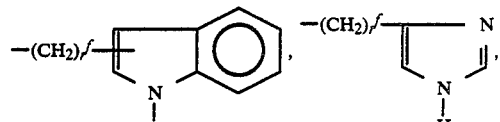
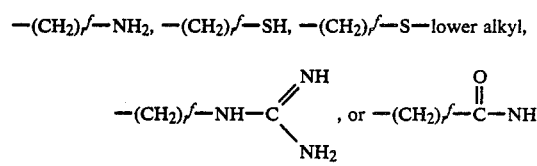
$r^f$ is an integer from 1 to 4,
$R_7{}^f$ is hydrogen, lower alkyl, halogen, keto, hydroxy,
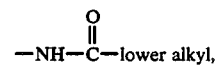
azido, amino,
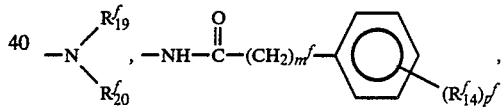
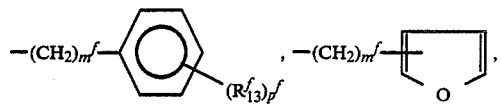
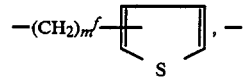
a 1- or 2-naphthyl of the formula
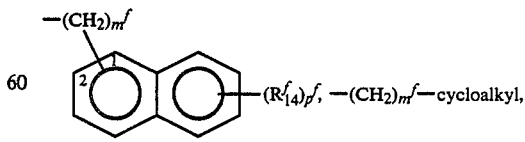, $-(CH_2)_m{}^f-$cycloalkyl,
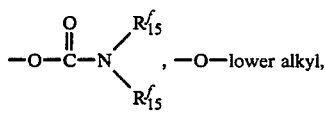, —O—lower alkyl, -continued

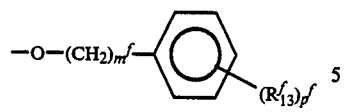

a 1- or 2-naphthyloxy of the formula

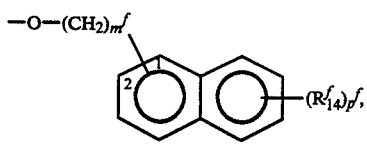

—S—lower alkyl,

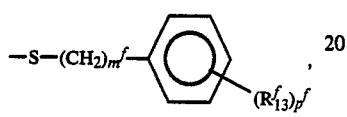

or a 1- or 2-naphthylthio of the formula

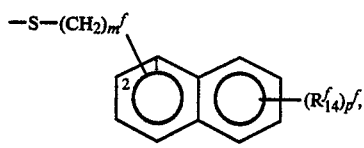

$R_8{}^f$ is keto, halogen,

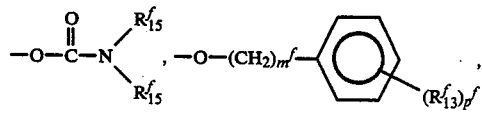

—O—lower alkyl, a 1- or 2-naphthyloxy of the formula

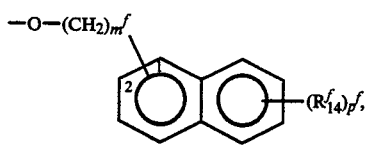

—S—lower alkyl,

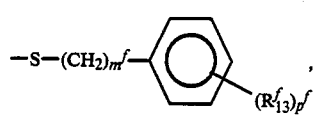

or a 1- or 2-naphthylthio of the formula

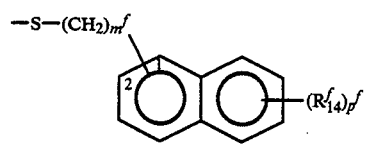

$R_9{}^f$ is keto or

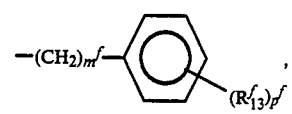

$R_{10}{}^f$ is halogen or $-Y^f-R_{16}{}^f$, $R_{11}{}^f$, $R_{11}{}^{f\prime}$, $R_{12}{}^f$ and $R_{12}{}^{f\prime}$ are independently selected from hydrogen and lower alkyl or $R_{11}{}^{f\prime}$, $R_{12}{}^f$ and $R_{12}{}^{f\prime}$ are hydrogen and $R_{11}{}^f$ is

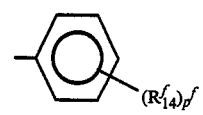

$R_{13}{}^f$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl, $R_{14}{}^f$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy, $m^f$ is zero, one, two, three, or four, $p^f$ is one, two or three provided that p is more than one only if $R_{13}{}^f$ or $R_{14}{}^f$ is hydrogen, methyl, methoxy, chloro, or fluoro, $R_{15}{}^f$ is hydrogen or lower alkyl of 1 to 4 carbons, $Y^f$ is oxygen or sulfur, $R_{16}{}^f$ is lower alkyl of 1 to 4 carbons,

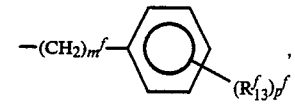

or the $R_{16}{}^f$ groups join to complete an unsubstituted 5- or 6-membered ring or said ring in which one or more
of the carbons has a lower alkyl of 1 to 4 carbons or a di(lower alkyl of 1 to 4 carbons) substituent, $R_{19}{}^f$ is lower alkyl, benzyl, or phenethyl, $R_{20}{}^f$ is hydrogen, lower alkyl, benzyl or phenethyl, $R_6{}^f$ is hydrogen, lower alkyl, benzyl, benzhydryl,

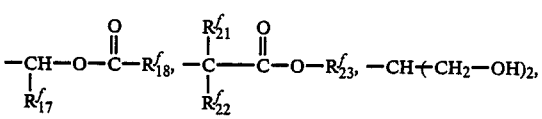

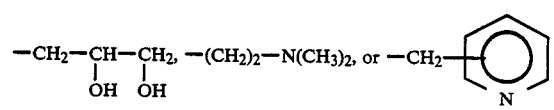

$R_{12}{}^f$ is hydrogen, lower alkyl, cycloalkyl, or phenyl, $R_{18}{}^f$ is hydrogen, lower alkyl, lower alkoxy, or phenyl or $R_{17}{}^f$ and $R_{18}{}^f$ taken together are $-(CH_2)_2-$, $-(CH_2)_3-$, $-CH=CH-$, or

$R_{21}{}^f$ and $R_{22}{}^f$ are independently selected from hydrogen and lower alkyl,
$R_{23}{}^f$ is lower alkyl,
$R_{24}{}^f$ is hydrogen, lower alkyl,

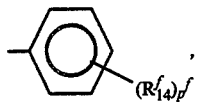

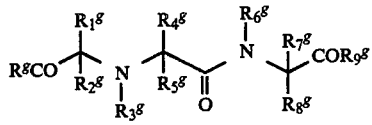

a compound of the formula

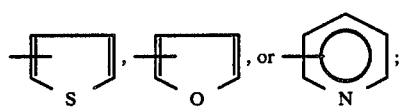

either (A) $R^g$ and $R_9{}^g$ are OH, 1-6C alkoxy, 2-6C alkenyloxy, di-(1-6C alkyl)amino-(1-6C) alkoxy, 1-6C hydroxyalkoxy, acylamino-(1-6C)alkoxy, acyloxy-(1-6C)alkoxy, aryloxy, aryloxy-(1-6C)alkoxy, NH$_2$, mono- or di-(1-6C alkyl)amino, hydroxyamino or aryl-(1-6C)alkylamino;

$R_1{}^g$-$R_5{}^g$, $R_7{}^g$ and $R_8{}^g$ are 1-20C alkyl, 2-20C alkenyl, 2-20C alkynyl, aryl, aryl-(1-6C) alkyl having 7-12C or heterocyclyl-(1-6C)alkyl having 7-12C;

$R_6{}^g$ is cycloalkyl, polycycloalkyl, partly saturated cycloalkyl or polycycloalkyl, cycloalkyl-(1-6C)alkyl having 3-20C, 6-10C aryl, aryl-(1-6C)alkyl, aryl-(2-6C)alkenyl or aryl-(2-6C)alkynyl; or $R_2{}^g$ and $R_3{}^g$ together with the C and N atoms to which they are attached or $R_3{}^g$ and $R_5{}^g$ together with the N and C atoms to which they are all alkyl, alkenyl and alkynyl are optionally substituted by OH, 1-6C alkoxy, thio(sic), 1-6C alkylthio, NH$_2$, mono- or di-(1-6C alkyl)amino, halogen or NO$_2$;

all 'cycloalkyl' groups (including poly and partially unsaturated) are optionally substituted by halogen, 1-6C hydroxyalkyl, 1-6C alkoxy, amino-(1-6C alkyl)amino, di-(1-6C alkyl)amino, SH, 1-6C alkylthio, NO$_2$ or CF$_3$; and aryl groups are optionally substituted by OH, 1-6C alkoxy, NH$_2$, mono- or di-(1-6C alkyl)amino, SH, 1-6C alkylthio, 1-6C hydroxyalkyl, 1-6C aminoalkyl, 1-6C thioalkyl, NO$_2$, halogen, CF$_3$, OCH$_2$O, ureido or guanidino;

or (B) $R^g$ and $R_9{}^g$ are H or 1-6C alkoxy;
$R_1{}^g$ and $R_2{}^g$ are H, 1-6C alkyl, aryl-(1-6C) alkyl having 7-12C or heterocyclyl-(1-6C) alkyl having 6-12C;
$R_3{}^g$-$R_5{}^g$, $R_7{}^g$ and $R_8{}^g$ are H or 1-6C alkyl;

$R_6{}^g$ is cycloalkyl, polycycloalkyl partly saturated cycloalkyl or polycycloalkyl, cycloalkyl-(1-6C) alkyl having 3-20C, aryl or aryl-(1-6C) alkyl; and aryl has 6-10C and is optionally substituted by 1-6C alkyl, 2-6C alkenyl, 2-6C alkynyl, OH, 1-6C alkoxy, NH$_2$, mono- or di-(1-6C alkyl)amino, SH, 1-6C alkylthio, 1-6C hydroxyalkyl, 1-6C aminoalkyl, 1-6C thioalkyl, NO$_2$, halogen, CF$_3$, OCH$_2$O, ureido or guanidino;

a compound of the formula

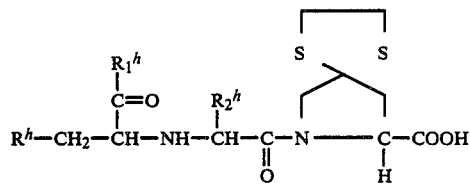

wherein
$R^h$ is lower alkyl, benzyl, benzylthio, benzyloxy, phenylthio or phenoxy;
$R_1{}^h$ is hydroxy or lower alkoxy;
$R_2{}^h$ is hydrogen, lower alkyl or amino lower alkyl; and the pharmaceutically acceptable salts thereof;
a compound of the formula

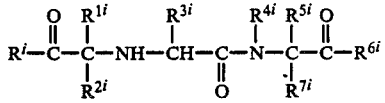

or a pharmaceutically acceptable salt thereof, wherein $R^i$ and $R^{6i}$ are the same or different and are hydroxy, lower alkoxy, lower alkenyloxy, dilower alkylamino lower alkoxy, acylamino lower alkoxy, acyloxy lower alkoxy, aryloxy, aryllower alkoxy, amino, lower alkylamino, dilower alkylamino, hydroxyamino, aryllower alkylamino, or substituted aryloxy or substituted aryllower alkoxy wherein the substitutent is methyl, halo or methoxy; $R^{1i}$ is hydrogen, alkyl of from 1 to 10 carbon atoms, substituted lower alkyl wherein the substitutent is hydroxy, lower alkoxy, aryloxy, substituted aryloxy, heteroaryloxy, substituted heteroaryloxy, amino, lower alkylamino, diloweralkylamino, acylamino, arylamino, substituted arylamino, guanidino, imidazolyl, indolyl, lower alkylthio, arylthio, substituted arylthio, carboxy, carbamoyl, lower alkoxy carbonyl, aryl, substituted aryl, aralkyloxy, substituted aralkyloxy, aralkylthio or substituted aralkylthio, wherein the aryl or heteroaryl portion of said substituted aryloxy, heteroaryloxy, arylamino, arylthio, aryl, aralkyloxy, aralkylthio group is substituted with a group selected from halo, lower alkyl, hydroxy, lower alkoxy, amino, aminomethyl, carboxyl, cyano, or sulfamoyl; $R^{2i}$ and $R^{7i}$ are the same or different and are hydrogen or lower alkyl; $R^{3i}$ is hydrogen, lower alkyl, phenyl lower alkyl, aminomethylphenyl lower alkyl, hydroxyphenyl lower alkyl, hydroxy lower alkyl, acylamino lower alkyl, amino lower alkyl, dimethylamino lower alkyl, guanidino lower alkyl, imidazolyl lower alkyl, indolyl lower alkyl, or lower alkyl thio lower alkyl; $R^{4i}$ and $R^{5i}$ are the same or different and are hydrogen, lower alkyl or $Z^i$, or $R^{4i}$ and $R^{5i}$ taken together form a group represented by $Q^i$, $U^i$, $V^i$, $Y^i$, $D^i$ or $E^i$, wherein;

$Z^i$ is

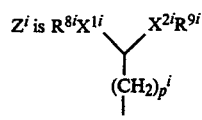

wherein $X^{1i}$ and $X^{2i}$ independent of each other are O, S or $CH_2$, $R^{8i}$ and $R^{9i}$ independent of each other are lower alkyl, lower alkenyl, lower alkynyl, cycloalkyl having 3 to 8 carbon atoms, hydroxy lower alkyl, or $-(CH_2)_{n^i}Ar^i$, wherein $n^i$ is 0, 1, 2 or 3 and $Ar^i$ is unsubstituted or substituted phenyl, furyl, thienyl or pyridyl, wherein said substituted phenyl, furyl, thienyl or pyridyl groups are substituted with at least one group that is independently selected from $C_1$ to $C_4$ alkyl, lower alkoxy, lower alkylthio, halo, $CF_3$ and hydroxy, or $R^{8i}$ and $R^{9i}$ taken together form a bridge $W^i$, wherein $W^i$ is a single bond or a methylene bridge or a substituted methylene bridge when at least one of $X^{1i}$ and $X^{2i}$ is methylene, or $W^i$ is an alkylene or substituted alkylene bridge having 2 or 3 carbon atoms, said substituted methylene bridge or said substituted alkylene bridge having one or two substituents selected from lower alkyl, aryl and aryl lower alkyl groups, and $p^i$ is 0, 1 or 2; with the proviso that at least one of $R^{4i}$ and $R^{5i}$ is $Z^i$, with the proviso that if $R^{4i}$ is $Z^i$ and $p^i$ is 0 then $X^{1i}$ and $X^{2i}$ must both be methylene, and with the proviso that if $X^{1i}$ and $X^{2i}$ are both methylene then $R^{8i}$ and $R^{9i}$ must form an alkylene bridge $W^i$;

$Q^i$ is

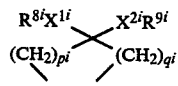

wherein $R^{8i}$, $R^{9i}$, $X^{1i}$ and $X^{2i}$ are as defined above, $p^i$ is 0, 1 or 2, $q^i$ is 0, 1 or 2, with the proviso that the sum of $p^i$ and $q^i$ must be 1, 2 or 3, with the proviso that if $p^i$ is 0 then $X^{1i}$ and $X^{2i}$ must be methylene, and with the proviso that if $X^{1i}$ and $X^{2i}$ are methylene then $R^{8i}$ and $R^{9i}$ taken together form a bridge $W^i$, wherein $W^i$ is as defined above;

$V^i$ is

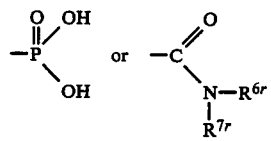

wherein $R^{8i}$, $R^{9i}$, $X^{1i}$ and $X^{2i}$ are as defined above, $p^i$ is 0, 1 or 2 and $q^i$ is 0, 1 or 2, with the proviso that the sum of $p^i$ and $q^i$ is 1, 2 or 3, with the proviso that if $X^{1i}$ and $X^{2i}$ are $CH_2$ then $R^{8i}$ and $R^{9i}$ taken together form a bridge $W^i$, wherein $W^i$ is as defined above;

$U^i$ is

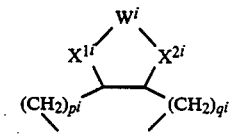

wherein $W^i$ is as defined above (except that $W^i$ may also be a methylene bridge when $X^{1i}$ and $X^{2i}$ are oxygen or sulfur), $X^{1i}$ and $X^{2i}$ are as defined above, $p^i$ is 0, 1 or 2, $q^i$ is 0, 1 or 2, with the proviso that the sum of $p^i$ and $q^i$ is 1 or 2, and with the proviso that if $p^i$ is 0, $X^{1i}$ must be $CH_2$;

$Y^i$ is

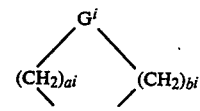

wherein $G^i$ is oxygen, sulfur or $CH_2$, $a^i$ is 2, 3 or 4 and b is 1, 2, 3, 4 or 5, with the proviso that the sum of $a^i$ and $b^i$ is 5, 6 or 7 or $G^i$ is $CH_2$, $a^i$ is 0, 1, 2 or 3, $b^i$ is 0, 1, 2 or 3 with the proviso that the sum of $a^i$ and $b^i$ is 1, 2 or 3, with the proviso that the sum of $a^i$ and $b^i$ may be 1, 2 or 3 only if $R^{1i}$ is lower alkyl substituted with aralkylthio or aralkyloxy;

$D^i$ is

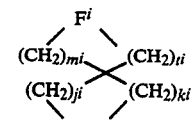

wherein $F^i$ is O or S, $j^i$ is 0, 1 or 2 and $k^i$ is 0, 1 or 2, with the proviso that the sum of $j^i$ and $k^i$ must be 1, 2 or 3, and $m^i$ is 1, 2 or 3 and $t^i$ is 1, 2 or 3, with the proviso that the sum of $m^i$ and $t^i$ must be 2, 3 or 4;

$E^i$ is

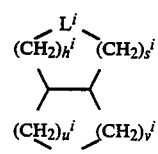

wherein $L^i$ is O or S, $u^i$ is 0, 1 or 2 and $v^i$ is 0, 1 or 2, with the proviso that the sum of $u^i$ and $v^i$ must be 1 or 2, and $h^i$ is 1 or 2 and $s^i$ is 1 or 2, with the proviso that the sum of $h^i$ and $s^i$ must be 2 or 3;

a compound of the formula

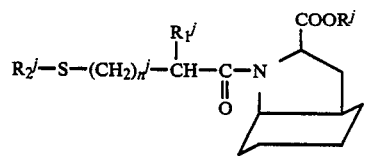

wherein $R^j$ is hydrogen or lower alkyl; $R_1{}^j$ is hydrogen, lower alkyl, or benzyl; $R_2{}^j$ is hydrogen or

wherein $R_3{}^j$ is lower alkyl, heteroaryl containing 4 to 9 carbon atoms and one of two nitrogen, oxygen or sulfur atoms; phenyl, substituted phenyl having 1 or 2 substituents selected from the group consisting of fluorine, chlorine, bromine, lower alkyl or alkoxy; and n is 0 or 1; wherein lower alkyl and lower alkoxy include straight or branched groups containing 1 to 4 carbon atoms, and pharmaceutically acceptable salts of the compounds when $R^j$ is hydrogen and when $R_3{}^j$ is heteroaryl containing 1 or 2 nitrogen atoms;
a compound of the formula

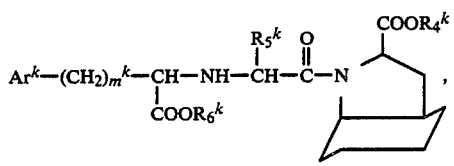

wherein $R_4{}^k$ is hydrogen or lower alkyl; $R_5{}^k$ is hydrogen, lower alkyl or benzyl; $R_6{}^k$ is hydrogen or lower alkyl; $Ar^k$ is phenyl or phenyl substituted with 1 or 2 substituents selected from the group consisting of fluorine, chlorine, bromine, lower alkyl, lower alkoxy, hydroxy or amino; and m is 0 to 3; wherein lower alkyl and lower alkoxy contain 1 to 4 straight or branched carbon atoms; and the pharmaceutcally acceptable salts thereof;
a compound of the formula

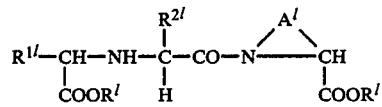

and

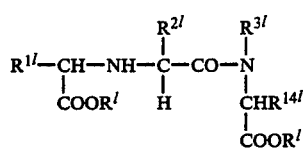

wherein:
$R^l$ and $R^{2l}$ are independently hydrogen; loweralkyl; aralkyl; or aryl;
$R^{1l}$ is hydrogen; branched or straight chain $C_{1-12}$ alkyl and alkenyl; $C_3$-$C_9$ cycloalkyl and benzofused alkyl; substituted loweralkyl where the substituents are halo, hydroxy loweralkoxy, aryloxy, amino, mono- or diloweralkylamino, acylamino, arylamino, guanidino, mercapto, loweralkylthio, arylthio, carboxy, carboxyamido, or loweralkoxycarbonyl; aryl; substituted aryl where the substituents are loweralkyl, loweralkoxy, or halo; arloweralkyl; arloweralkenyl; heteroarloweralkyl; heteroarloweralkenyl; substituted arloweralkyl, substituted arloweralkenyl, substituted heteroarloweralkyl, or substituted heteroarloweralkenyl where the aryl and heteroaryl substituents are halo, dihalo, loweralkyl, hydroxy, loweralkoxy, amino, aminoloweralkyl, acylamino, mono- or diloweralkylamino, carboxyl, haloloweralkyl, nitro, cyano, or sulfonamido, and where the loweralkyl portion of arloweralkyl may be substituted by amino, acylamino, or hydroxyl;

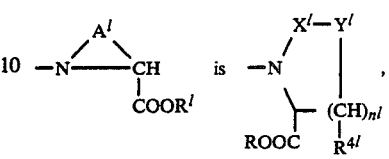

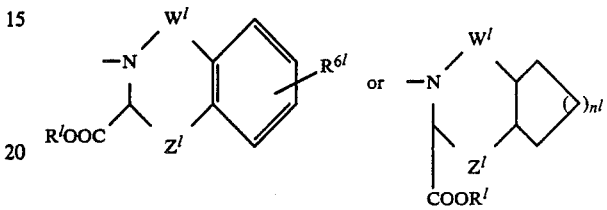

where
$X^l$ and $Y^l$ taken together are —CH$_2$—CH$_2$—;

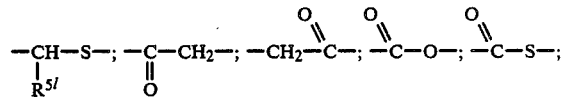

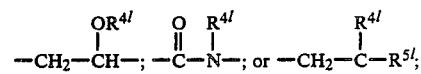

$R^{4l}$ is hydrogen; loweralkyl; aryl; substituted aryl;
$R^{5l}$ is hydrogen; loweralkyl; aryl or substituted aryl;
$n^l$ is 1 to 3;
$W^l$ is absent; —CH$_2$—; or

$Z^l$ is $+CH_2)_{\overline{m}l}$, where m is 0 to 2, provided that $m^l$ may not be 0 and $W^l$ may not be absent at the same time; and
$R^{6l}$ is hydrogen; loweralkyl; halo; or $OR^{4l}$;

$R^{2l}$ is —CH$_2)_{rl}B^l$—CH$_2)_{sl}NR^{7l}R^{15l}$ where
$r^l$ and $s^l$ are independently 0 to 3;
$B^l$ is absent; —O—; —S—; or —NR$^{8l}$—; where $R^{8l}$ is hydrogen; loweralkyl; alkenoyl; or aroyl; and
$R^{7l}$ is

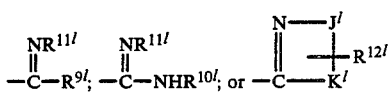

where
$R^{9l}$ is loweralkyl; aralkyl; aryl; heteroaryl; or heteroarloweralkyl and these groups substituted by hydroxy, lower alkoxy or halo; carboxyl; carboxamido; nitromethenyl;
$R^{10l}$ is hydrogen; loweralkyl; aryl; or amidino;
$R^{11l}$ is hydrogen; loweralkyl; cyano; amidino; aryl; aroyl; loweralkanoyl;

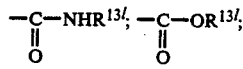

—NO$_2$; —SO$_2$NH$_2$; or SO$_2$R$^{13l}$;

R$^{12l}$ is hydrogen; loweralkyl; halo; aralkyl; amino; cyano; mono- or diloweralkylamino; or OR$^{4l}$;

R$^{13l}$ is hydrogen; loweralkyl; or aryl;

R$^{15l}$ is hydrogen; lower alkyl; aralkyl; or aryl;

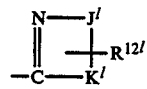

constitute a basic heterocycle of 5 or 6 atoms or benzofused analogs thereof and optionally containing 1–3N atoms, an oxygen, a sulfur, an S=O, or an SO$_2$ group optionally substituted by amino, lower alkyl amino, diloweralkyl amino, lower alkoxy, or aralkyl groups;

R$^{3l}$ is C$_{3-8}$ cycloalkyl and benzofused C$_{3-8}$ cycloalkyl; perhydrobenzofused C$_{3-8}$ cycloalkyl; aryl; substituted aryl; heteroaryl; substituted heteroaryl;

R$^{14l}$ is hydrogen or loweralkyl; and, a pharmaceutically acceptable salt thereof;

a compound of the formula

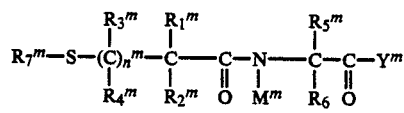

wherein

R$_1^m$, R$_2^m$, R$_3^m$, R$_4^m$, R$_5^m$ and R$_6^m$ are hydrogen, alkyl, alkenyl, alkynyl, phenyl-alkyl, and cycloalkyl, and may be the same or different, n$^m$ is an integer from 0 to 4 inclusive, M$^m$ is alkenyl, alkynyl, cycloalkyl, cycloalkyl-alkyl, polycycloalkyl, polycycloalkyl-alkyl, aryl, aralkyl, heteroaryl, heteroaryl-alkyl, hetero-cycloalkyl, hetero-cycloalkyl-alkyl, fused aryl-cycloalkyl, fused aryl-cycloalkyl-alkyl, fused heteroaryl-cycloalkyl, fused heteroaryl-cycloalkyl-alkyl, alkoxyalkyl, alkylthioalkyl, alkylamino-alkyl, or dialkylaminoalkyl, Y$^m$ is hydroxy, alkoxy, amino, or substituted amino aminoalkanoyl, aryloxy, aminoalkoxy, or hydroxyalkoxy, and R$_7^m$ is hydrogen, alkanoyl, carboxyalkanoyl, hydroxyalkanoyl, aminoalkanoyl, cyano, amidino, carbalkoxy, Z$^m$S or

wherein Z$^m$ is hydrogen, alkyl, hydroxyalkyl, or the radical

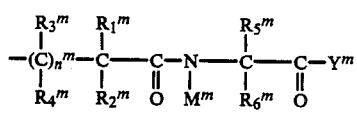

wherein R$_1^m$, R$_2^m$, R$_3^m$, R$_4^m$, R$_5^m$, R$_6^m$, n$^m$, M$^m$ and Y$^m$ are as described above; and where Y is hydroxy, their non-toxic, pharmaceutically acceptable alkali metal, alkaline earth metal, and amine salts;

a compound of the formula

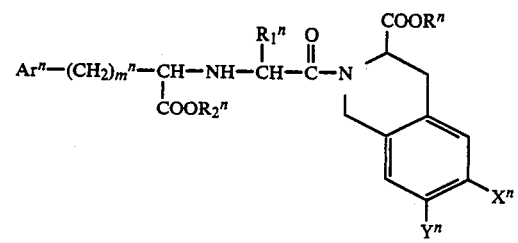

wherein R$^n$ is hydrogen, lower alkyl or aralkyl; R$_1^n$ is hydrogen, lower alkyl, or benzyl; R$_2^n$ is hydrogen or lower alkyl, and Ar$^n$ is phenyl or phenyl substituted with 1 or 2 substituents selected from the group consisting of fluorine, chlorine bromine, lower alkyl, lower alkoxy, hydroxy or amino; X$^n$ and Y$^n$ are independently hydrogen, lower alkyl, lower alkoxy, lower alkylthio, lower alkylsulfinyl, lower alkylsulfonyl, hydroxy, or X$^n$ and Y$^n$ together are methylenedioxy; m$^n$ is 0 to 3; and the pharmaceutically acceptable acid salts thereof;

a compound of the formula

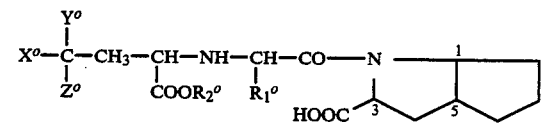

hydrogen atoms at ring positions 1 and 5 are cis to each other and the 3-carboxy group has the endo orientation;

R$_1^o$ is H, allyl, vinyl or the side chain of an optionally protected naturally occurring a-amino acid;

R$_2^o$ is H, 1–6C alkyl, 2–6C alkenyl or aryl(1–4C alkyl);

Y$^o$ is H or OH and Z$^o$ is H, or Y$^o$ and Z$^o$ together oxygen;

X$^o$ is 1–6C alkyl, 2–6C alkenyl, 5–9C cycloalkyl, 6–12C aryl (optionally substituted by one to three 1–4C alkyl or alkoxy, OH, halo, nitro, amino (optionally substituted by one or two 1–4C alkyl), or methylenedioxy) or indol-3-yl);

a compound of the formula

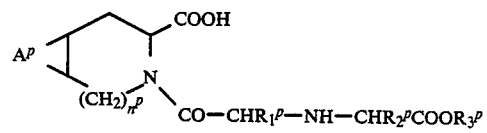

n$^p$ is 0 or 1;

is a benzene or cyclohexane ring;

$R_1^p$ and $R_2^p$ are each 1-6C alkyl, 2-6C alkenyl, 5-7C cycloalkyl, 5-7C cycloalkenyl, 7-12C cycloalkylalkyl, optionally partially hydrogenated 6-10C aryl, 7-14C aralkyl or 5-7 membered monocyclic or 8-10 membered bicyclic heterocyclyl containing 1 or 2 S or O and/or 1-4N atoms; all $R_1^p$ and $R_2^p$ groups are optionally substituted, $R_3^p$ is H, 1-6C alkyl, 2-6C alkenyl or 7-14C aralkyl;

a compound of the formula

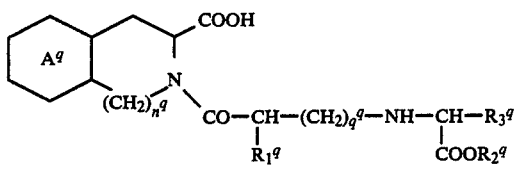

wherein:

the ring $A^q$ is saturated and $n^q=0$ or 1, or the ring $A^q$ is a benzene ring and $n^q=1$, $R_1^q$ represents a lower alkyl group having from 1 to 4 carbon atoms which can carry an amino group, $R_2^q$ represents a hydrogen atom or a alkyl group having from 1 to 4 carbon atoms, $R_3^q$ represents a straight or branched alkyl group, a mono- or dicycloalkylalkyl or phenylalkyl group having no more than a total of 9 carbon atoms, or a substituted alkyl group of the formula:

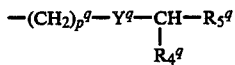

with $R_4^q=H$, a lower alkyl ($C_1$ to $C_4$) or a cycloalkyl ($C_3$ to $C_6$) group, $R_5^q=H$, a lower alkyl ($C_1$ to $C_4$) a cycloalkyl ($C_3$ to $C_6$) or an alkoxycarbonyl group, $Y^q=S$ or $>N-Q^q$ where $Q^q=H$, or an acetyl or benzyloxycarbonyl group, and $p^q32$ 1 or 2, and $q^q=0$ or 1, and the pharmaceutically acceptable salts thereof;

a compound of the formula

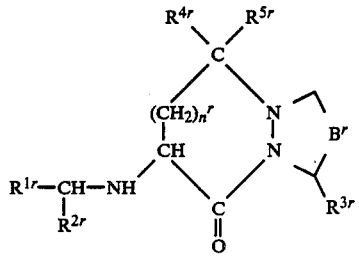

wherein $B^r$ represents a methylene (—CH$_2$—), ethylene (—CH$_2$—CH$_2$—) or vinylene (—CH═CH—) group, $R^{1r}$ represents a hydrogen atom or an alkyl, aralkyl, aminoalkyl, monoalkylaminoalkyl, dialkylamino-alkyl, acylamino-alkyl, phthalimido-alkyl, alkoxycarbonylaminoalkyl, aryloxycarbonyl-amino-alkyl, aralkoxycarbonylamino-alkyl, alkylaminocarbonylaminoalkyl, arylaminocarbonylamino-alkyl, aralkylaminocarbonylamino-alkyl, alkylsulphonylamino-alkyl or arylsulphonylamino-alkyl group, $R^{2r}$ represents a carboxyl, alkoxycarbonyl or aralkoxycarbonyl group or a group of the formula

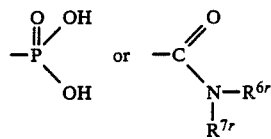

$R^{3r}$ represents a carboxyl, alkoxycarbonyl or aralkoxycarbonyl group, $R^{4r}$ and $R^{5r}$ each represent a hydrogen atom or $R^{4r}$ and $R^{5r}$ together represent an oxo group, $R^{6r}$ and $R^{7r}$ each represent a hydrogen atom or an alkyl or aralkyl group or $R^{6r}$ and $R^{7r}$ together with the nitrogen atom to which they are attached represent a saturated 5 membered or 6-membered heteromonocyclic ring which may contain a further nitrogen atom or an oxygen or sulphur atom, and $n^r$ stands for zero, 1 or 2, and pharmaceutically acceptable salts thereof; a compound of the formula

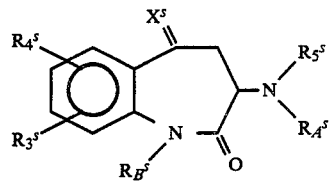

wherein $R_A^s$ and $R_B^s$ are radicals of the formula

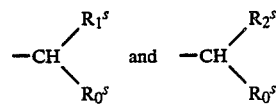

respectively in which $R_0^s$ is carboxy or a functionally modified carboxy;

$R_1^s$ is hydrogen, lower alkyl, amino(lower)alkyl, aryl, aryl (lower) alkyl, cycloalkyl or cycloalkyl (lower) alkyl;

$R_2^s$ is hydrogen or lower alkyl;

$R_3^s$ and $R_4^s$, each independently, represent hydrogen, lower alkyl, lower alkoxy, lower alkanoyloxy, hydroxy, halogen, trifluoromethyl, or $R_3^s$ and $R_4^s$ taken together represent lower alkylenedioxy;

$R_5^s$ is hydrogen or lower alkyl, and $X^s$ represents oxo, two hydrogens, or one hydroxy together with one hydrogen; and wherein the carbocyclic ring may also be hexahydro or 6,7,8,9-tetrahydro, and salts and complexes thereof; and a compound of the formula

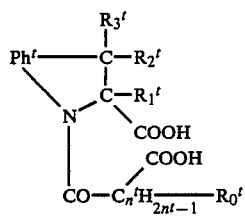

wherein Ph' is unsubstituted 1,2-phenylene, or 1,2-phenylene substituted by one to three identical or different members selected from lower alkyl, lower alkoxy, lower alkylenedioxy, hydroxy, halogeno and trifluoromethyl; $R_0'$ is hydrogen or HPh'; each of $R_1'$, $R_2'$ and $R_3'$ is hydrogen or lower alkyl; and $n'$ is an integer from 1 to 10; the amides, mono- or di-lower alkylamides, lower alkyl esters, (amino, mono- or di-lower alkylamino, carboxy or lower carbalkoxy)-lower alkyl esters, or pharmaceutically acceptable salts thereof.

12. A method of claim 10 wherein the neutral metalloendopeptidase inhibitor is chosen from:

N-[N-[L-1-(2,2-dimethyl-1-oxopropoxy)methoxy]-carbonyl]-2-phenylethyl]-L-phenylalanyl]-β-alanine(2,2-dimethyl-1-oxopropoxy)methyl ester;

N-[N-[(L-1-carboxy-2-phenylethyl)]-L-phenylalanyl]-β alanine;

N-[1-oxo-3-phenyl-2-(phosphonomethyl)propyl]-β-alanine; and

N-[1-oxo-3-phenyl-2-(phosphonomethyl)propyl]-β-alanine ethyl ester.

13. A method of claim 11 wherein the neutral metalloendopeptidase inhibitor is chosen from:

N-[N-[L-1-(2,2-dimethyl-1-oxopropoxy)methoxy]-carbonyl]-2-phenylethyl]-L-phenylalanyl]-β-alanine(2,2-dimethyl-1-oxopropoxy)methyl ester;

N-[N-[(L-1-carboxy-2-phenylethyl)]-L-phenylalanyl]-β alanine;

N-[1-oxo-3-phenyl-2-(phosphonomethyl)propyl[-β-alanine; and

N-[1-oxo-3-phenyl-2-(phosphonomethyl)propyl]-β-alanine ethyl ester.

14. A method of claim 10 wherein the neutral metalloendopeptidase inhibitor is administered at a dosage level of 1 to 100 mg/kg mammalian weight per day and the angiotensin converting enzyme inhibitor is administered at a dosage level of 0.1 to 30 mg/kg mammalian weight per day.

15. A kit comprising in separate containers in a single package pharmaceutical compositions for use in combination to treat hypertension in mammals which comprises in one container a pharmaceutical composition comprising 10 to 500 mg per dose of a neutral metalloendopeptidase inhibitor and in a second container, a pharmaceutical composition comprising 0.001 to 1 mg per dose of an atrial peptide.

16. A kit comprising in separate containers in a single package pharmaceutical composition for use in combination to treat hypertension in mammals which comprises in one container a pharmaceutical composition comprising 10 to 500 mg per dose of a neutral metalloendopeptidase inhibitor and in a second container, a pharmaceutical composition comprising 5 to 50 mg per dose of an angiotensin converting enzyme inhibitor.

* * * * *